(12) United States Patent
Kasumi et al.

(10) Patent No.: US 9,635,343 B2
(45) Date of Patent: Apr. 25, 2017

(54) STEREOSCOPIC ENDOSCOPIC IMAGE PROCESSING APPARATUS

(71) Applicant: OLYMPUS CORPORATION, Hachioji-shi, Tokyo (JP)

(72) Inventors: Makoto Kasumi, Hachioji (JP); Masashi Umemura, Hamburg (DE); Shusuke Tsuchiya, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/162,713

(22) Filed: May 24, 2016

(65) Prior Publication Data
US 2016/0269713 A1 Sep. 15, 2016

Related U.S. Application Data

(63) Continuation of application No. PCT/JP2014/077917, filed on Oct. 21, 2014.

(30) Foreign Application Priority Data

Jan. 24, 2014 (JP) ................................ 2014-011746

(51) Int. Cl.
*H04N 13/00* (2006.01)
*G06T 1/00* (2006.01)
(Continued)

(52) U.S. Cl.
CPC ....... *H04N 13/0051* (2013.01); *A61B 1/0002* (2013.01); *A61B 1/00009* (2013.01);
(Continued)

(58) Field of Classification Search
CPC . A61B 1/00193; A61B 1/0009; A61B 1/0005; G02B 23/2415; G02B 27/22;
(Continued)

(56) References Cited

U.S. PATENT DOCUMENTS

2012/0271102 A1  10/2012  Katayama
2013/0051660 A1  2/2013  Shibuhisa et al.
(Continued)

FOREIGN PATENT DOCUMENTS

EP   2550909 A1   1/2013
JP   2004-065804 A   3/2004
(Continued)

OTHER PUBLICATIONS

Jan. 27, 2015 International Search Report issued in International Patent Application No. PCT/JP2014/077917.
(Continued)

*Primary Examiner* — Edward Park
(74) *Attorney, Agent, or Firm* — Oliff PLC

(57) ABSTRACT

A stereoscopic endoscopic image processing apparatus includes: a synchronization adjustment portion that performs a synchronization adjustment between a left-eye image signal and a right-eye image signal; an image analysis portion that analyzes a region that an image of a treatment instrument occupies in a peripheral region around a central region in an image of one image signal; a blur region setting portion that, with respect to the image in the peripheral region around the central region in which blur processing is not performed, sets a region in which to perform blur processing in accordance with an analysis result of the image analysis portion; and an image compositing portion that composites and outputs a 3D image with respect to which blur processing is performed on the left-eye image and the right-eye image, respectively, in accordance with a setting result of the blur region setting portion.

17 Claims, 16 Drawing Sheets

(51) Int. Cl.
  *A61B 1/00* (2006.01)
  *G02B 23/24* (2006.01)
  *H04N 13/02* (2006.01)
  *G06T 7/00* (2017.01)
  *H04N 7/18* (2006.01)

(52) U.S. Cl.
  CPC ...... *A61B 1/00193* (2013.01); *G02B 23/2415* (2013.01); *G06T 1/00* (2013.01); *G06T 7/0081* (2013.01); *G06T 7/0085* (2013.01); *H04N 13/004* (2013.01); *H04N 13/0037* (2013.01); *H04N 13/0239* (2013.01); *G06T 2207/10012* (2013.01); *G06T 2207/10068* (2013.01); *H04N 7/18* (2013.01)

(58) Field of Classification Search
  CPC ...... G06T 2207/10068; G06T 2210/41; H04N 13/0239; H04N 13/004
  See application file for complete search history.

(56) References Cited

U.S. PATENT DOCUMENTS

| | | | | |
|---|---|---|---|---|
| 2013/0076858 | A1* | 3/2013 | Moon | H04N 13/026 348/43 |
| 2014/0125778 | A1* | 5/2014 | Kim | H04N 13/026 348/51 |
| 2014/0210945 | A1* | 7/2014 | Morizumi | A61B 1/00096 348/45 |
| 2015/0077529 | A1 | 3/2015 | Hatta et al. | |
| 2015/0235373 | A1* | 8/2015 | Kato | G06T 7/0075 348/51 |

FOREIGN PATENT DOCUMENTS

| | | |
|---|---|---|
| JP | 2011-082829 A | 4/2011 |
| JP | 2011-250059 A | 12/2011 |
| WO | 2011/148921 A1 | 12/2011 |
| WO | 2013/187116 A1 | 12/2013 |

OTHER PUBLICATIONS

Nov. 10, 2015 Office Action issued in Japanese Patent Application No. 2015-538792.

Feb. 9, 2016 Decision to Grant a Patent issued in Japanese Patent Application No. 2015-538792.

Feb. 2, 2017 Extended European Search Report issued in EP 14879713.7.

* cited by examiner

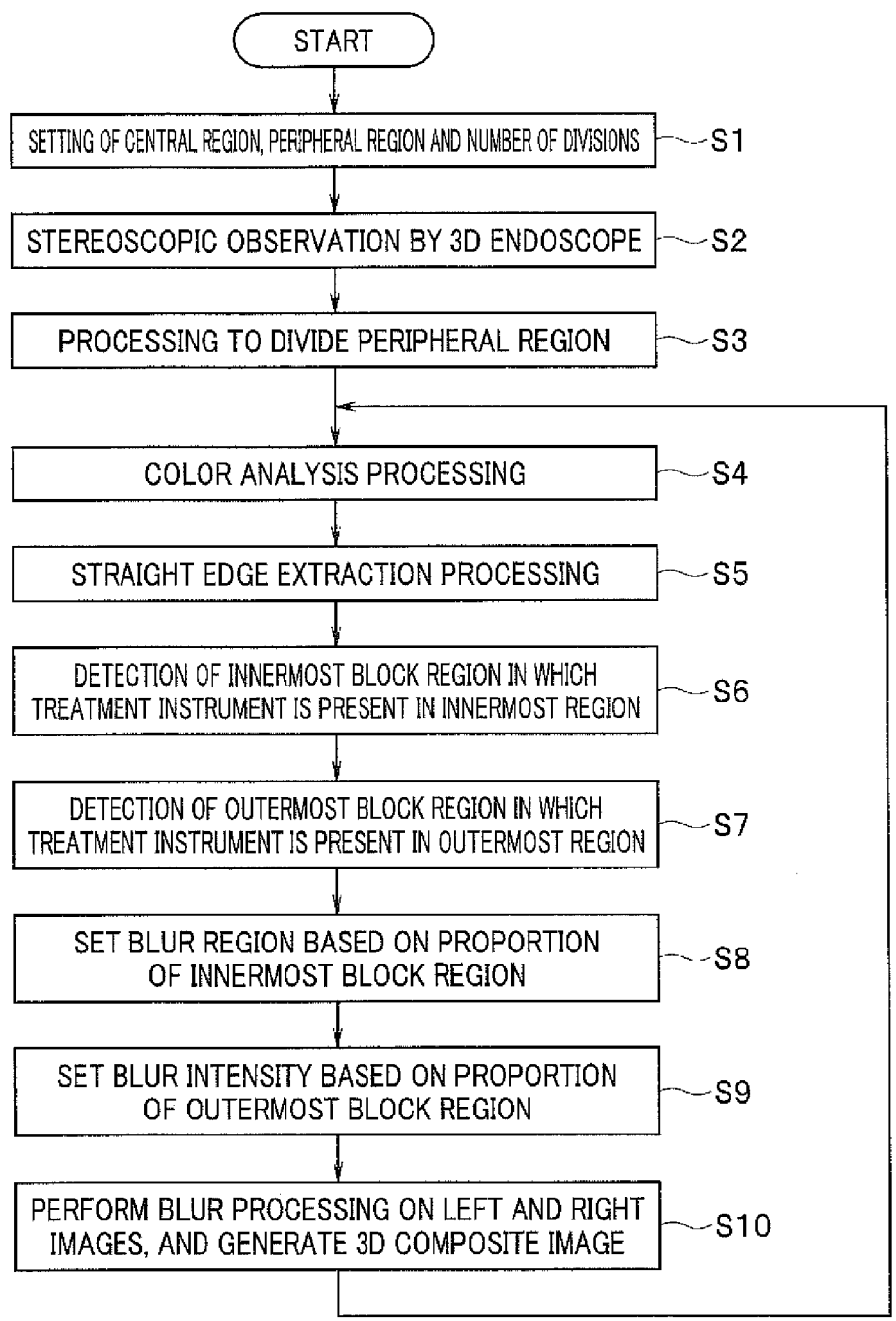

STEREOSCOPIC ENDOSCOPIC IMAGE PROCESSING APPARATUS

CROSS REFERENCE TO RELATED APPLICATION

This application is a continuation application of PCT/JP2014/077917 filed on Oct. 21, 2014 and claims benefit of Japanese Application No. 2014-011746 filed in Japan on Jan. 24, 2014, the entire contents of which are incorporated herein by this reference.

BACKGROUND OF THE INVENTION

1. Field of the Invention

The present invention relates to a stereoscopic endoscopic image processing apparatus that performs image processing on left and right image signals obtained by a stereoscopic endoscope.

2. Description of the Related Art

Endoscopes are being widely used in recent years in the fields of medical treatment and the like. When performing surgery or the like that requires a high degree of precision, in some cases it is difficult to perceive the relevant site or the like with a normal endoscope that uses a single image pickup device, and therefore a stereoscopic endoscope is used with a stereoscopic sense (sense of depth) can be perceived with respect to the depth direction.

In the case of using a stereoscopic endoscope, an image processing apparatus is used that performs image processing on left and right image signals that are obtained by left and right image pickup devices, and outputs a generated stereoscopic image signal to a display portion or a display apparatus.

A conventional example of such kind of image processing apparatus is disclosed in Japanese Patent Application Laid-Open Publication No. 2011-82829, which discloses an image processing apparatus that performs larger blur processing on a peripheral region than on a central region in a right-eye image or a left-eye image. Further, Japanese Patent Application Laid-Open Publication No. 2011-82829 also discloses setting a larger blur intensity as the amount of deviation between a right-eye image and a left-eye image increases. Performing blur processing in this manner facilitates recognition by an observer of a stereoscopic image that formed by fusing a right-eye image and left-eye image.

SUMMARY OF THE INVENTION

A stereoscopic endoscopic image processing apparatus according to one aspect of the present invention includes: a synchronization adjustment portion configured to perform a synchronization adjustment between a left-eye image signal that represents a left-eye image and a right-eye image signal that represents a right-eye image, based on output signals of left and right image pickup devices provided in a stereoscopic endoscope; an image analysis portion configured to analyze a region that an image of a treatment instrument occupies in a peripheral region around a central region in an image of at least one image signal among the left-eye image signal and the right-eye image signal; a blur region setting portion configured to, with respect to the image in the peripheral region that is disposed around an image in the central region in which blur processing is not performed, set a blur region as a region in which to perform blur processing in accordance with an analysis result of the image analysis portion; and an image compositing portion configured to composite and output a 3D image with respect to which blur processing is performed on the left-eye image and the right-eye image, respectively, in accordance with a synchronization adjustment result of the synchronization adjustment portion and a setting result of the blur region setting portion.

BRIEF DESCRIPTION OF THE DRAWINGS

FIG. 7 is a flowchart illustrating processing contents that correspond to typical operations of the first embodiment;

DETAILED DESCRIPTION OF THE PREFERRED EMBODIMENTS

Hereunder, embodiments of the present invention are described with reference to the drawings.

(First Embodiment)

Figure 1:
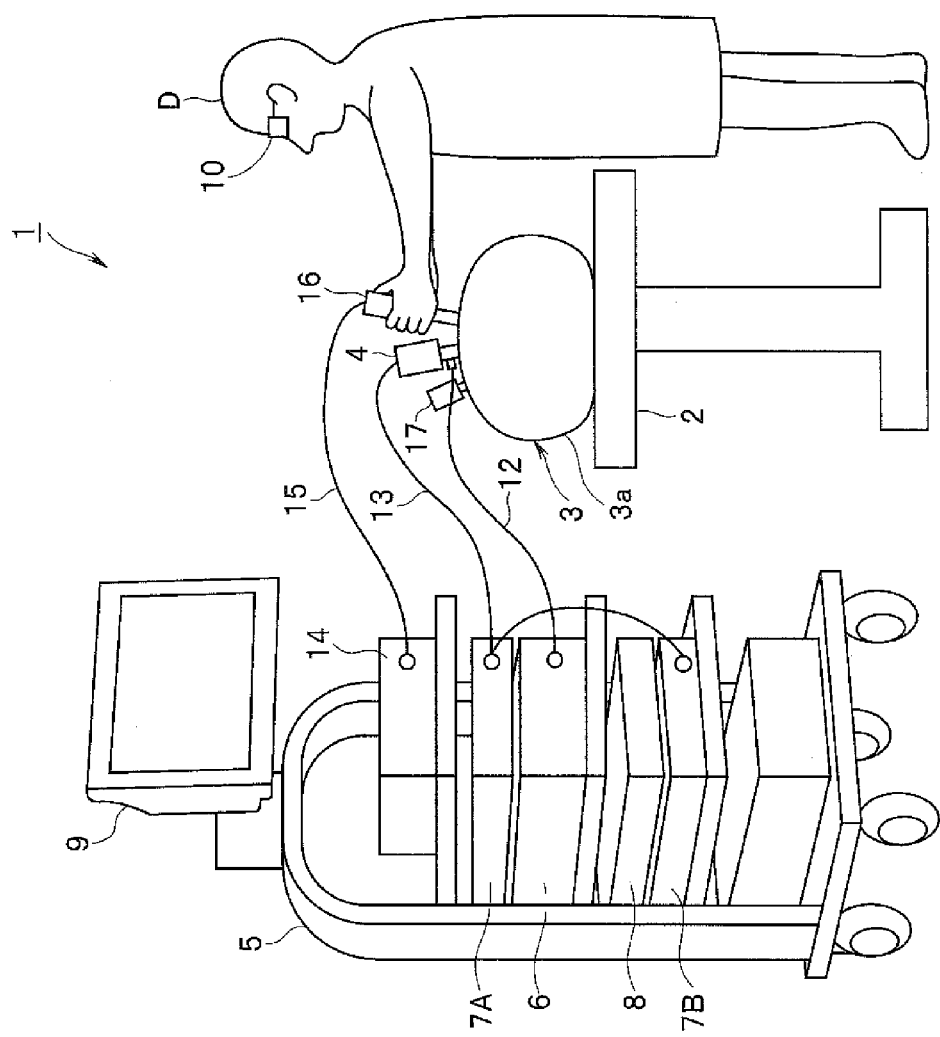
FIG. 1 is a view illustrating the overall configuration of a stereoscopic endoscope apparatus that is equipped with a first embodiment of the present invention.

As shown in FIG. 1, a stereoscopic endoscope apparatus 1 equipped with a stereoscopic endoscopic image processing apparatus of the present invention includes a stereoscopic endoscope (abbreviated as "3D endoscope") 4 that is used to perform stereoscopic observation with respect to a patient 3 lying on an operating table 2 inside an operating room, and a plurality of medical instruments that are mounted on a trolley 5.

A light source apparatus 6 that generates an illuminating light, a first processor 7A that generates a left-eye image signal, a second processor 7B that generates a right-eye image signal, a three-dimension mixer (abbreviated as "3D mixer") 8 as an image generation apparatus that generates a three-dimensional (3D) image signal for stereoscopic (3D) observation based on first and second image signals from the two processors 7A and 7B, a 3D monitor 9 that displays a 3D image signal that is generated by the 3D mixer 8, and 3D glasses 10 that a doctor D wears, for example, to stereoscopically view an image for stereoscopic (3D) observation that is displayed on the 3D monitor 9 are arranged as a plurality of medical instruments on a trolley 5.

Figure 2:
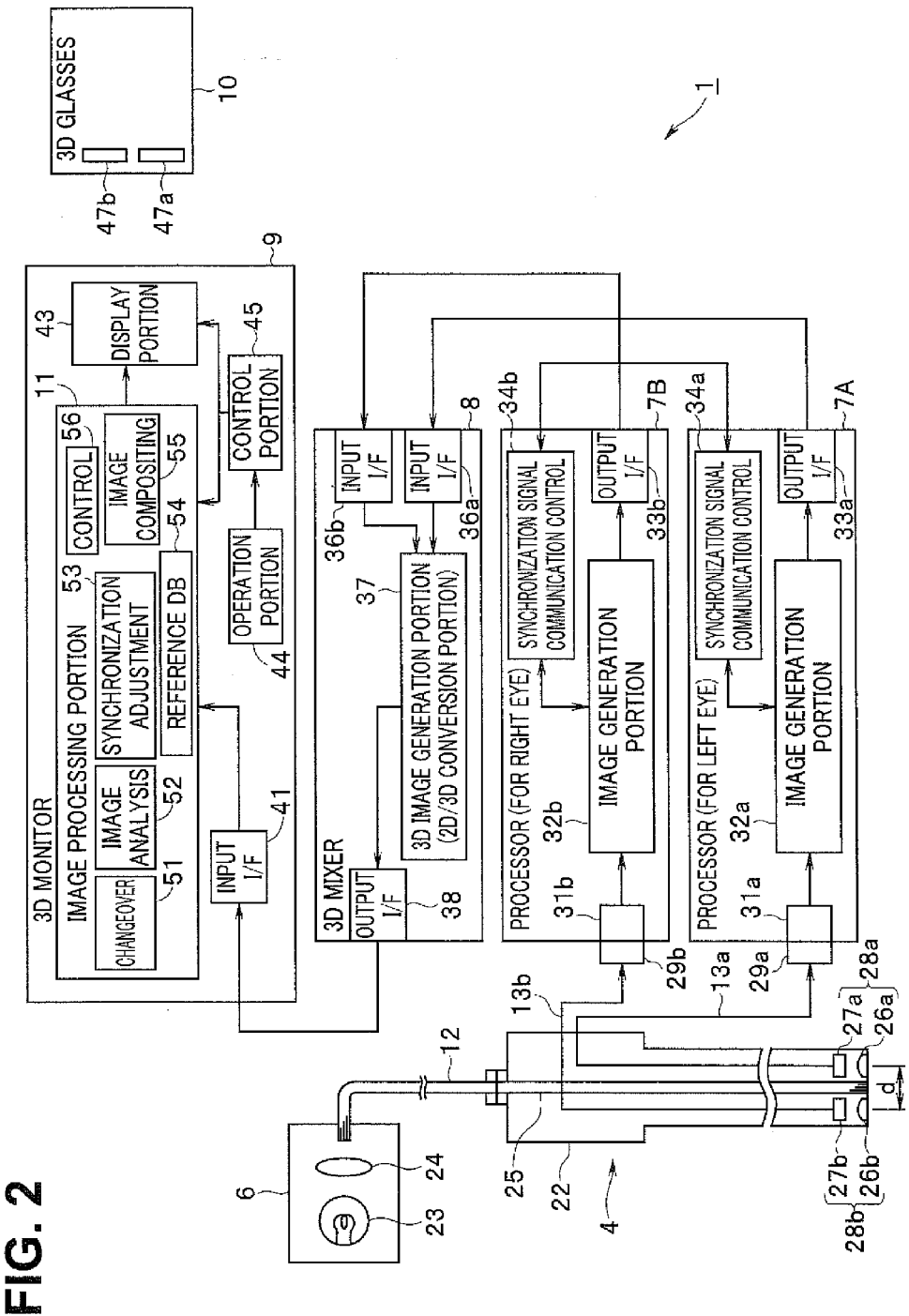
FIG. 2 is a view illustrating the internal configuration of a stereoscopic endoscope apparatus including a 3D monitor that is equipped with an image processing portion of the first embodiment.

In the present embodiment, an image processing portion (or image processing circuit) 11 constituting the stereoscopic endoscopic image processing apparatus of the present invention is provided inside the 3D monitor 9 (see FIG. 2). The first processor 7A and the second processor 7B are also referred to as a processor for the left eye and a processor for the right eye. In FIG. 2, the first processor 7A and the second processor 7B are shown as a processor (for left eye) and a processor (for right eye). Note that the stereoscopic endoscopic image processing apparatus is not limited to a case of an image processing portion 11 (or 11B that is described later), and may also be formed by a stereoscopic endoscope apparatus 1 (or 1B that is described later).

The 3D endoscope 4 that is inserted through an unshown trocar into, for example, an abdominal area 3a of the patient 3 is connected through a light guide cable 12 with the light source apparatus 6. The 3D endoscope 4 is also connected to the processors 7A and 7B through a signal cable 13 (note that, as shown in FIG. 2, the 3D endoscope 4 may be connected to the processors 7A and 7B through two signal cables 13a and 13b).

An electric scalpel power source apparatus or an electric scalpel apparatus 14 is mounted on the trolley 5. When using, for example, an electric scalpel 16 as a treatment instrument, the electric scalpel power source apparatus or electric scalpel apparatus 14 supplies a high frequency signal to the electric scalpel 16 through an electric scalpel cable 15.

A treatment instrument 17 that is operated by an unshown assistant is also inserted into the abdominal area 3a of the patient 3. The assistant operates the treatment instrument 17 to enable the surgery performed by the doctor D to be smoothly performed. Note that, although in FIG. 1 the treatment instrument denoted by reference numeral 17 is shown as being separate to the electric scalpel 16 as a treatment instrument, the treatment instrument denoted by reference numeral 17 may be a plurality of treatment instruments 17a, 17b and 17c as shown in FIG. 6B and the like. FIG. 2 illustrates the internal configurations of the main medical instruments shown in FIG. 1.

The 3D endoscope 4 has an insertion portion 21 that is inserted into the body, a grasping portion 22 that is provided at a rear end (proximal end) of the insertion portion 21 and is grasped by the doctor D or an assistant, and a light guide cable 12 and signal cables 13a and 13b that are extended from the grasping portion 22. An end portion of the light guide cable 12 is detachably connected to the light source apparatus 6.

The light source apparatus 6 has a lamp 23 that generates a white illuminating light, and a condenser lens 24 that condenses illuminating light and makes light incident on (supplies light to) the end portion of the light guide cable 12. The illuminating light that enters the light guide cable 12 is made incident on an end portion on a proximal end side of a light guide 25 that is inserted through the insertion portion 21. The light guide 25 transmits the illuminating light that is incident on the end portion on the proximal end side thereof to an end portion on a distal end side of the light guide 25, and emits the illuminating light from an illuminating window in which a distal end face of the light guide 25 is arranged, to thereby illuminate an object such as an in-vivo lesion portion.

A left-eye objective lens 26a and a right-eye objective lens 26b for forming optical images of an object are arranged so as to be separate from each other by a distance d in the transverse direction in the distal end portion of the insertion portion 21. At the respective image forming positions thereof are arranged an image pickup surface of a left-eye charge coupled device (abbreviated as "CCD") 27a as an image pickup device for the left eye, and an image pickup surface of a right-eye CCD 27b as an image pickup device for the right eye.

Note that, in the present description, the term "left image pickup device" is used with the same meaning as "image pickup device for a left eye", and likewise the term "right image pickup device" is used with the same meaning as "image pickup device for a right eye", and the terms "left" and "right" are also used with a similar meaning for items other than image pickup devices. For example, the terms "left-eye image signal" and "right-eye image signal" have the same meaning as the term "left and right image signals".

The left and right CCDs 27a and 27b output image pickup signals as output signals obtained by photoelectric conversion of optical images obtained by forming an image of an object. A left-eye image pickup portion or a left image pickup portion (left image pickup device) 28a is formed by the left-eye objective lens 26a and the left-eye CCD 27a, and a right-eye image pickup portion or a right image pickup portion (right image pickup device) 28b is formed by the right-eye objective lens 26b and the right-eye CCD 27b. By picking up images of the same object that have the aforementioned distance d therebetween by means of the two image pickup portions 28a and 28b which have different line-of-sight directions to each other, and displaying an image for 3D observation on the 3D monitor 9 as a display apparatus, the doctor D (as an observer) that observes the image for 3D observation can perceive a three-dimensional sensation or depth sensation when observing each part of the object.

A signal connector 29a of the CCD 27a which is provided at a rear end thereof is detachably connected to a signal connector bracket 31a of the first processor 7A through a signal cable 13a that is inserted through the 3D endoscope 4 and extended to outside thereof. A signal connector 29b of the CCD 27b which is provided at a rear end thereof is detachably connected to a signal connector bracket 31b of the second processor 7B through a signal cable 13b that is inserted through the 3D endoscope 4 and extended to outside thereof.

The first processor 7A includes an image generation portion (or image generation circuit) 32a that generates a two-dimensional (2D) image signal for the left eye based on an image pickup signal for the left eye that is generated by the CCD 27a, an image output interface (in FIG. 2, abbreviated as "output I/F") 33a that outputs a 2D image signal that is generated by the image generation portion 32a, and a synchronization signal communication portion (or synchronization signal communication circuit) 34a that carries out communication of synchronization signals when generating a 2D image signal. A 2D image signal for the left eye that is generated by the image generation portion 32a is outputted to the 3D mixer 8 through the image output interface 33a.

Similarly, the second processor 7B includes an image generation portion (or image generation circuit) 32b that generates a two-dimensional (2D) image signal for the right eye based on an image pickup signal for the right eye that is generated by the CCD 27b, an image output interface (output I/F) 33b that outputs a 2D image signal for the right eye that is generated by the image generation portion 32b, and a synchronization signal communication portion (or synchronization signal communication circuit) 34b that carries out communication of synchronization signals when generating a 2D image signal. A 2D image signal for the right eye that is generated by the image generation portion 32b is outputted to the 3D mixer 8 through the image output interface 33b.

The synchronization signal communication portions 34a and 34b send a synchronization signal from one thereof to the other thereof, and the other synchronization signal communication portion to which the synchronization signal is sent generates a synchronization signal that is synchronized with the synchronization signal that is sent thereto. In other words, after carrying out communication, the two synchronization signal communication portions 34a and 34b enter a state in which the two synchronization signal communication portions 34a and 34b generate the same synchronization signal, and the two image generation portions 32a and 32b enter a state in which the two image generation portions 32a and 32b generate a 2D image signal for the left eye and a 2D image signal for the right eye, respectively, that are synchronized with the same synchronization signal.

Note that the image generation portions 32a and 32b may be configured to include the image output interfaces 33a and 33b, respectively.

The 3D mixer 8 includes: image input interfaces (abbreviated as "input I/F" in FIGS. 2) 36a and 36b into which a 2D image signal for the left eye and a 2D image signal for the right eye that are generated by the two image generation portions 32a and 32b, respectively, are inputted; a 3D image generation portion (or 3D image generation circuit) 37 that generates a 3D image signal (or video signal) based on a 2D image signal for the left eye and a 2D image signal for the right eye that are inputted from the two image input interfaces 36a and 36b; and an image output interface ("output I/F" in FIG. 2) 38 that outputs the generated 3D image signal to an external 3D monitor 9.

The 3D image generation portion 37, for example, compresses to a multiple of ½ the cycle of the two 2D image signals that are inputted, to thereby double the display rate. Further, the 3D image generation portion 37 generates a 3D image signal that has the 2D image signal for the left eye in a first field (odd-numbered field) of half of a single frame period with respect to the 2D image signal, and has the 2D image signal for the right eye in a second field (even-numbered field). In other words, the 3D image generation portion 37 can also be referred to as a 2D/3D conversion portion (or 2D/3D conversion circuit) that converts left and right 2D image signals into a 3D image signal.

The 3D monitor 9 includes: an image input interface (input I/F) 41a into which a 3D image signal is inputted; an image processing portion 11 that performs image processing which analyzes a region in which a treatment instrument (in the description of the configuration in FIG. 1, the treatment instrument 17 and a treatment instrument that is represented by the electric scalpel 16 are denoted by different reference numerals; however, since the treatment instruments are not detected as different kinds of treatment instrument when performing image processing, hereunder, treatment instruments are denoted by reference numerals 17a, 17b and 17e in the case of clearly indicating that there are a plurality of treatment instruments 17) exists in a peripheral region in left and right images, on the basis of a 3D image signal (video signal) generated based on left and right image pickup images (also referred to simply as "images") that are picked up by the left and right image pickup devices, and generates a 3D composite image signal in which blur processing is executed with respect to the image of the treatment instrument 17 in the relevant region; a display portion (or display panel) 43 that displays a 3D composite image signal that is generated; an operation portion (or operation circuit) 44 that performs an operation to set image processing parameters or the like of the image processing portion 11; and a control portion (or control circuit) 45 that performs control of the image processing portion 11 and the display portion 43.

Further, the doctor D that observes a 3D image that is displayed on the display screen of the display portion 43 of the 3D monitor 9 uses 3D glasses 10 having left and right polarizers 47a and 47b through which light passes in directions that are orthogonal to each other immediately in front of the left and right eyes.

Figure 3:
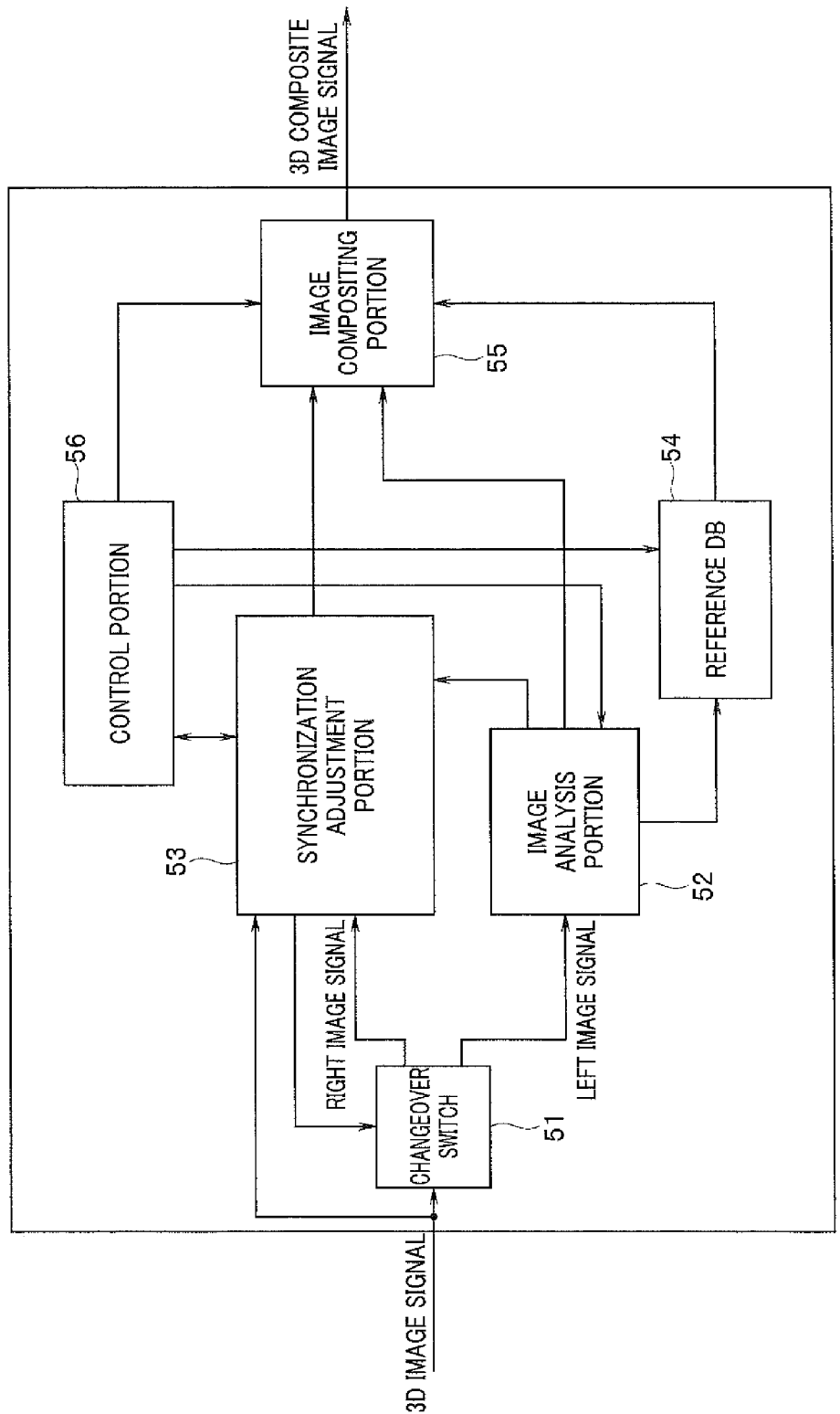
FIG. 3 is a block diagram illustrating the configuration of the image processing portion of the first embodiment.

FIG. 3 illustrates the configuration of the image processing portion 11. The image processing portion 11 includes: a changeover switch 51 constituting a separation portion (or separation circuit) that separates a 3D image signal into left and right image signals; an image analysis portion (or image analysis circuit) 52 that analyzes a region that the treatment instrument 17 occupies in an image of one of the image signals (in this case, the left image signal) into which the 3D image signal is separated by the changeover switch 51; a synchronization adjustment portion (or synchronization adjustment circuit) 53 that performs a synchronization adjustment between the one image signal and the other image signal (in this case, the right image signal); a reference DB (blur information reference DB) 54 that forms a database device (abbreviated as "DB") that stores blur information as information for performing blur processing in accordance with an analysis result of the image analysis portion 52; an image compositing portion (or image compositing circuit) 55 that outputs a 3D composite image signal as a 3D image signal with respect to which blur processing in accordance blur information corresponding to an analysis result of the image analysis portion 52 was performed on the one image signal and the other image signal that were subjected to a synchronization adjustment; and a control portion (or control circuit) 56 that controls the image analysis portion 52, the synchronization adjustment portion 53, the reference DB 54 and the image compositing portion 55 based on a timing signal of the synchronization adjustment portion 53.

Note that the aforementioned synchronization adjustment portion 53 can also be referred to as a "timing adjustment portion" (or timing adjustment circuit) that performs a timing adjustment so as to cause a 3D composite image signal obtained by synchronizing and performing blur processing on one of the image signals and the other of the image signals, respectively, to be outputted.

Figure 4:
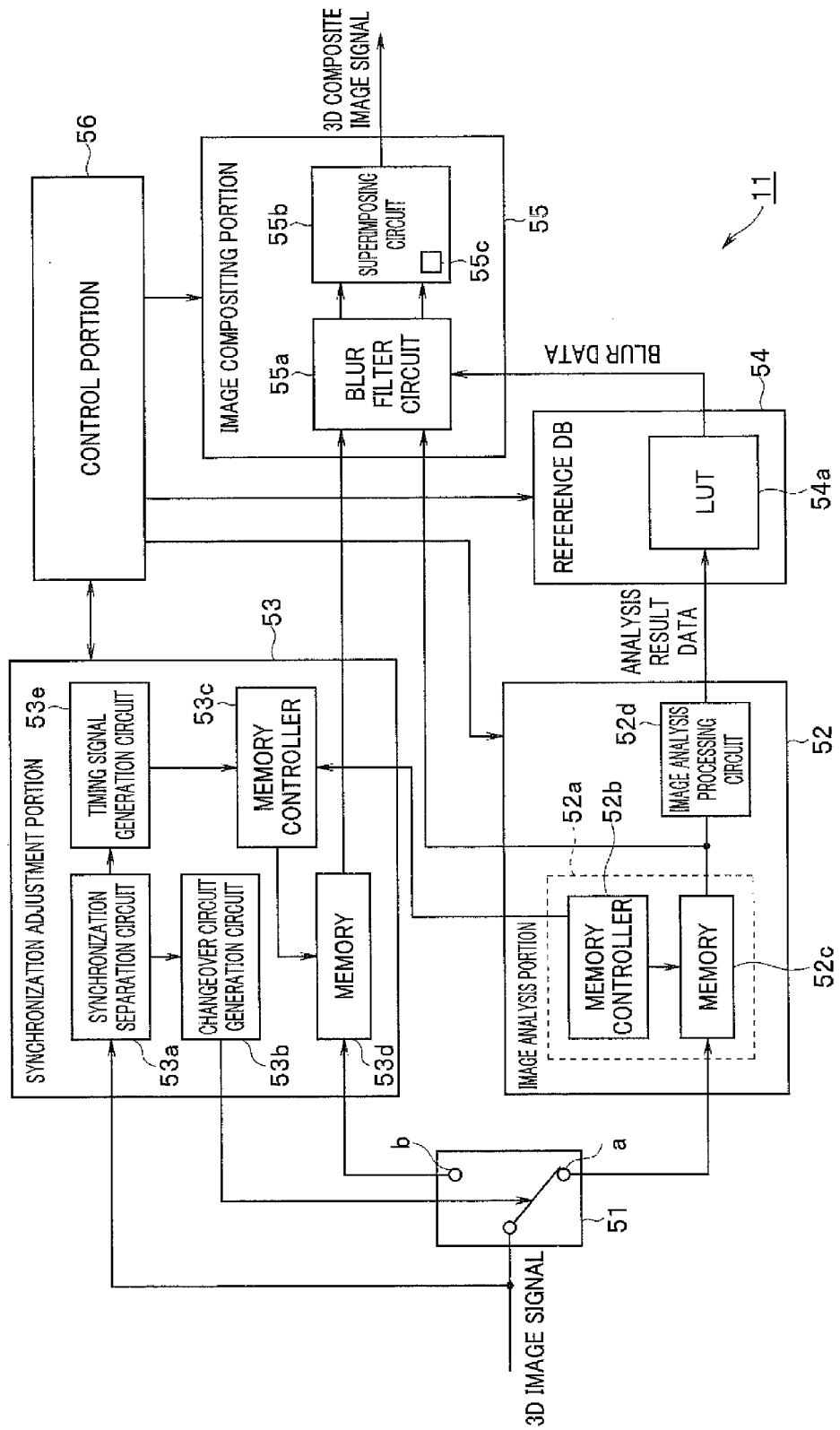
FIG. 4 is a block diagram illustrating the configuration of the image processing portion in further detail.

FIG. 4 illustrates a more detailed configuration of the image processing portion 11 shown in FIG. 3.

A 3D image signal that is inputted from the 3D mixer 8 is inputted to the changeover switch 51, and is also inputted to a synchronization separation circuit 53a of the synchronization adjustment portion 53. The synchronization separation circuit 53a extracts a synchronization signal from the 3D image signal. The synchronization signal is then inputted to a changeover signal generation circuit 53b which generates a changeover signal that becomes H or L for each field of half of one frame that is synchronized with the synchronization signal, and the changeover switch 51 to which the 3D image signal is inputted is changed over by the changeover signal.

A left image signal that is outputted, for example, for each odd-numbered field from a contact point a of the changeover switch 51 is inputted to the image analysis portion 52, and a memory controller 52b inside a capture circuit 52a constituting the image analysis portion 52 stores a left image signal for a single frame in a memory 52c.

A right image signal that is outputted, for example, for each even-numbered field from a contact point b of the changeover switch 51 is inputted to the synchronization adjustment portion 53, and a memory controller 53c inside the synchronization adjustment portion 53 stores a right image signal for a single frame in a memory 53d.

The synchronization adjustment portion 53 includes a timing signal generation circuit 53e that generates a timing signal that is synchronized with the synchronization signal. The memory controller 53c controls read/write operations with respect to the memory 53d in accordance with the timing signal that the timing signal generation circuit 53e outputs. The timing signal that the timing signal generation circuit 53e generates is also outputted to the image analysis portion 52, the image compositing portion 55 and the control portion 56 that are outside the synchronization adjustment portion 53 to thereby enable the performance of operations that are synchronized with the timing signal (illustration of output lines for the timing signal that is outputted to outside the synchronization adjustment portion 53 is omitted in FIG. 4, with the exception of an output line through which the timing signal is outputted to the control portion 56).

The image analysis portion 52 includes an image analysis processing circuit 52d forming an image analysis processing portion that, with respect to an image of a left image signal that is stored in the aforementioned memory 52c, performs image analysis processing that analyzes a region that the treatment instrument 17 occupies in a peripheral region around a central region in the relevant image.

The configuration and operations of the image analysis processing circuit 52d are described in further detail later with reference to FIG. 5. Further, the aforementioned central region and peripheral region are described later using FIG. 6A.

The image analysis processing circuit 52d outputs analysis result data that is generated by image analysis processing to the reference DB 54. The reference DB 54 is equipped with, for example, a look-up table (abbreviated as "LUT") 54a so that, taking the analysis result data as input data, the reference DB 54 outputs blur data corresponding to the input data. Accordingly, the reference DB 54 generates or outputs blur data corresponding to the analysis result data. The reference DB 54 outputs the blur data to a blur filter circuit 55a within the image compositing portion 55.

The image compositing portion 55 includes the blur filter circuit 55a that forms a blur processing portion that performs blur filter processing according to the blur data, and a superimposing circuit (or compositing circuit) 55b that, with respect to two image signals obtained by performing blur processing by means of the blur filter circuit 55a on image signals that are read out from the memories 52c and 53d and inputted, divides the two image signals into odd-numbered fields and even-numbered fields to superimpose (add) and combine the image signals. The superimposing circuit 55b also has a memory 55c that temporarily stores image signals that are subjected to blur filter processing by the blur filter circuit 55a. Note that a configuration may also be adopted in which the memory 55c is provided in the blur filter circuit 55a.

When the blur filter circuit 55a is set to a state in which blur filter processing is enabled by input of the blur data, the (memory controller 52b of the) image analysis portion 52 reads a left image signal from the memory 52c and causes the left image signal to be inputted into the blur filter circuit 55a of the image compositing portion 55. Further, when reading of the left image signal from the memory 52c ends, the (memory controller 52b of the) image analysis portion 52 sends a signal indicating the end of the read operation to the (memory controller 53c of the) synchronization adjustment portion 53, and the (memory controller 53c of the) synchronization adjustment portion 53 reads a right image signal from the memory 53d and causes the right image signal to be inputted into the blur filter circuit 55a of the image compositing portion 55.

Note that the (memory controller 53c of the) synchronization adjustment portion 53 reads a right image signal from the memory 53d and outputs the right image signal to the image compositing portion 55 while taking into account a time period that is required for image analysis from after the end of the operation to read the left image signal (in other words, the time that image analysis starts), and a time period that is required for blur processing.

Further, as described above, the blur filter circuit 55a performs blur processing sequentially on the left and right image signals that are read from the memories 52c and 53d and inputted thereto, and outputs the resulting signals to the superimposing circuit 55b. Note that a configuration may also be adopted in which, at a timing at which the image analysis processing circuit 52d of the image analysis portion 52 ends image analysis, the image analysis processing circuit 52d sends a signal indicating that image analysis ended to the (memory controller 53c of the) synchronization adjustment portion 53, and the (memory controller 53c of the) synchronization adjustment portion 53 performs a synchronization adjustment (or timing adjustment) so as to read a right image signal from the memory 53d and output the right image signal to the image compositing portion 55 while taking into account a time period that is required for blur processing with respect to the image of the left image signal.

Alternatively, a configuration may be adopted in which, at a timing at which blur processing with respect to the image of the left image signal ends, the blur filter circuit 55a sends a signal indicating that blur processing ended to the (memory controller 53c of the) synchronization adjustment portion 53, and upon receiving the aforementioned signal, the (memory controller 53c of the) synchronization adjustment portion 53 performs a synchronization adjustment (or timing adjustment) that reads a right image signal from the memory 53d and outputs the right image signal to the image compositing portion 55.

The superimposing circuit 55b performs blur processing sequentially with respect to left and right image signals that are sequentially inputted at timings within a single field, temporarily stores the left and right image signals that underwent blur processing in the memory 55c inside the superimposing circuit 55b, and thereafter, by performing a timing adjustment and reading out signals so that left and right image signals are respectively outputted at intervals of a single field, outputs a 3D composite image signal in which the left and right image signals are combined to the display portion 43. Therefore, a synchronization adjustment portion that performs synchronization adjustment of left and right image signals which constitutes the image processing portion 11 can also be regarded as being constituted by the synchronization adjustment portion 11 and the memory 55c that are shown in FIG. 4.

Note that, as described later, in a case where the blur filter circuit 55a is constituted by two blur filter circuits, a configuration may be adopted that causes left and right image signals to be outputted simultaneously from the memories 52c and 53d.

Figure 5:
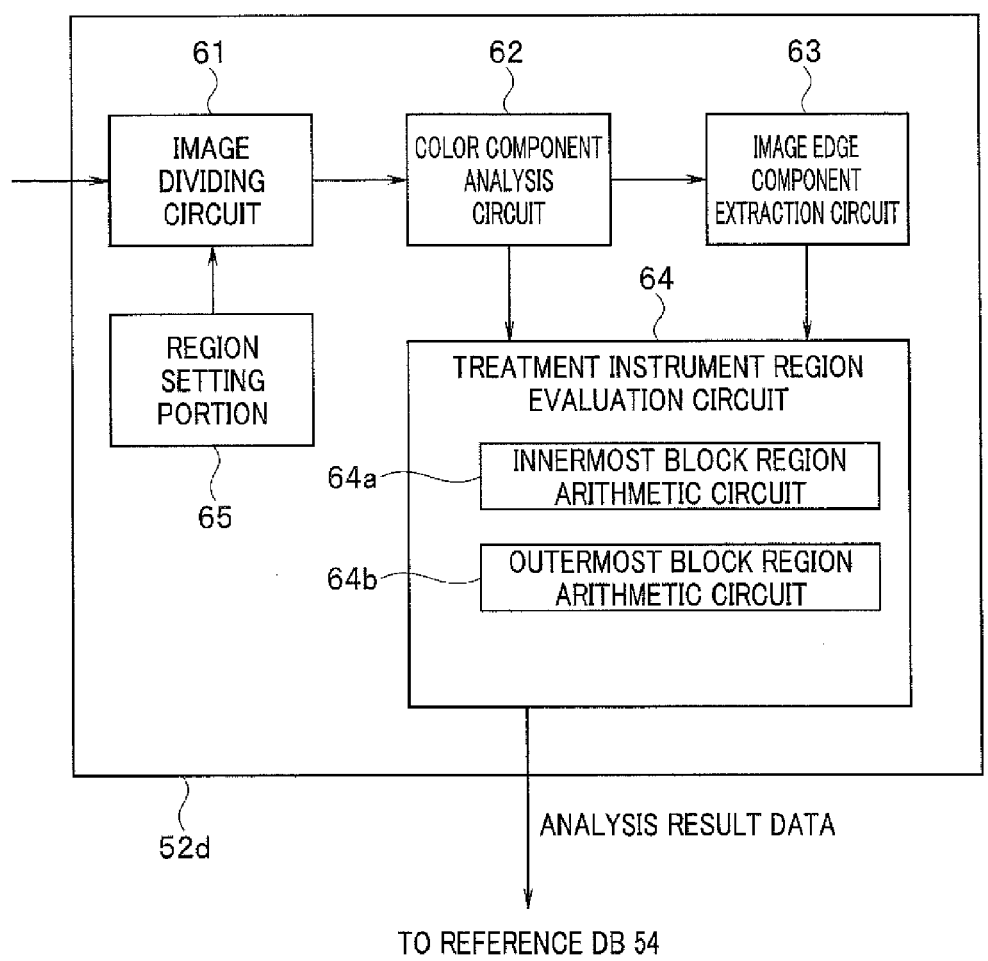
FIG. 5 is a block diagram illustrating the configuration of an image analysis processing circuit.

The image analysis processing circuit 52d illustrated in FIG. 5 includes: an image dividing circuit 61 forming an image dividing portion that divides (or segments) an image of a left image signal into a plurality of regions so as to be a predetermined number of regions for performing image analysis; a color component analysis circuit 62 forming a color component analysis portion that analyzes color components inside each region into which the aforementioned image is divided; an image edge component extraction circuit 63 forming an image edge component extraction portion that extracts an edge component of a straight component inside each region into which the aforementioned image is divided; and a treatment instrument region evaluation circuit 64 forming a treatment instrument region evaluation portion that evaluates a size (number of blocks or regions) of a region that an image of the treatment instrument 17 occupies in a peripheral region based on an analysis result of the color component analysis circuit 62 and an extraction result of the image edge component extraction circuit 63.

Figure 6A:
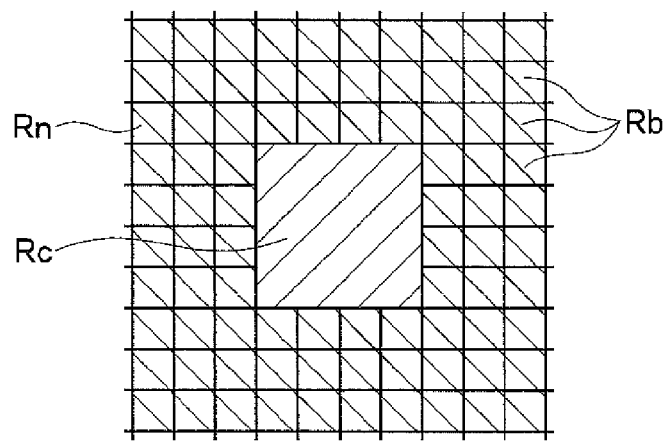
FIG. 6A is a view illustrating the manner in which a peripheral region around a central region in a left image is divided into a plurality of small regions.
Figure 6B:
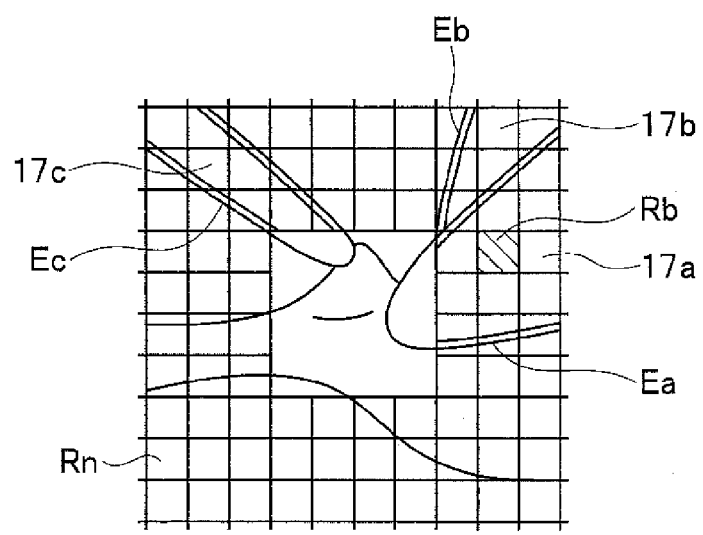
FIG. 6B is a view illustrating the manner in which color analysis and edge detection are performed in the peripheral region.

The aforementioned image dividing circuit 61, as shown in FIG. 6A, divides the entire region of an image of a left image signal into a central region Rc and a surrounding region or peripheral region Rn that is around the central region Rc, and also divides the peripheral region Rn into, for example, regions Rb having a number of divisions N as a plurality of regions Rb. Note that FIG. 6A clearly illustrates the central region Rc, the peripheral region Rn and the plurality of regions Rb in a state in which an image is not shown in order to clearly show the central region Rc, the peripheral region Rn and the plurality of regions Rb, while in FIG. 6B to FIG. 6D an image in a case where a plurality of treatment instruments 17a, 17b and 17c are present in the image is shown. As described above, in the present description, in a case where the need to emphasize (clearly indicate) the presence of the plurality of treatment instruments 17a, 17b and 17c is not high, the plurality of treatment instruments 17a, 17b and 17c are represented by the treatment instrument 17.

A user can set the size of the central region Re, for example, from a region setting portion (or region setting device) 65 provided in the image analysis processing circuit 52d using a keyboard or a mouse or the like. That is, the region setting portion 65 is constituted by a keyboard or a mouse or the like. Note that the region setting portion 65 may also be provided outside the image analysis processing circuit 52d.

When the central region Re is set, a region on the outside thereof becomes the peripheral region Rn. Further, in a case of setting a plurality of regions Rb with respect to the peripheral region Rn from the region setting portion 65, a user such as the doctor D can freely set the number and size thereof.

Note that the central region Rc is an image region in which visual characteristics of stereoscopic observation in a clear image state are desired by the doctor. In contrast, the demand for visual characteristics of stereoscopic observation in a clear image state in the peripheral region Rn formed so as to surround the outer side of the central region Re is low in comparison to the central region Re.

Consequently, in the present embodiment, image analysis is performed with regard to the existence of an image of the treatment instrument 17 in the peripheral region Rn, and at least an image portion of the treatment instrument 17 that is present in the peripheral region Rn is blurred based on the result of the image analysis to thereby suppress or reduce a factor that decreases the visual characteristics of stereoscopic observation that is due to (an image of) the treatment instrument 17 in a case where the (image of) the treatment instrument 17 is present in the peripheral region Rn, while maintaining the visual characteristics of stereoscopic observation in the central region Re.

In order to evaluate the size of an image of the treatment instrument 17 that is present in the peripheral region Rn, as shown in FIG. 6B, the color component analysis circuit 62 performs color analysis and the image edge component extraction circuit 63 extracts edge components Ea, Eb and Ec (described later).

Further, for example, the treatment instrument region evaluation circuit 64 includes: an innermost block region arithmetic circuit 64a that, based on an evaluation result of the treatment instrument region evaluation circuit 64, detects blocks of a region in which the treatment instrument 17 is present in an innermost region Rni that is a region on the innermost side in the peripheral region Rn, as an innermost block region Rnit (see FIG. 6C), and performs an arithmetic operation on the innermost block region Rnit (to calculate a proportion thereof in the innermost region Rni); and an outermost block region arithmetic circuit 64b that, based on an evaluation result of the treatment instrument region evaluation circuit 64, detects blocks of a region in which the treatment instrument 17 is present in an outermost region Rno that is a region on the outermost side in the peripheral region Rn, as an outer most block region Rnot (see FIG. 6D), and performs an arithmetic operation on the outermost block region Rnot (to calculate a proportion thereof in the outermost region Rno).

Figure 6C:
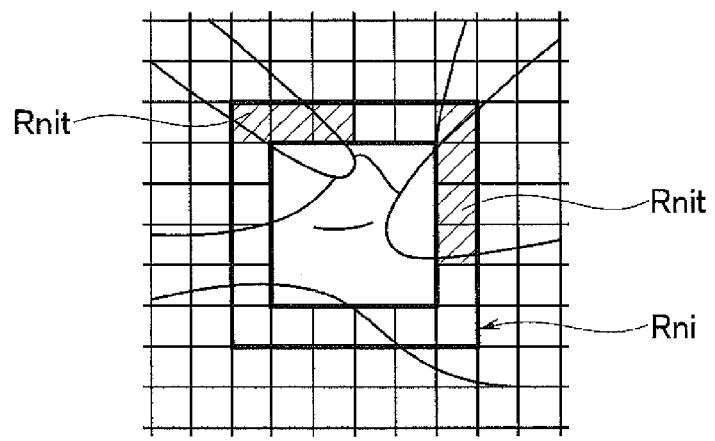
FIG. 6C is a view illustrating an innermost block region as a region in which a treatment instrument is present in an innermost region of the peripheral region.
Figure 6D:
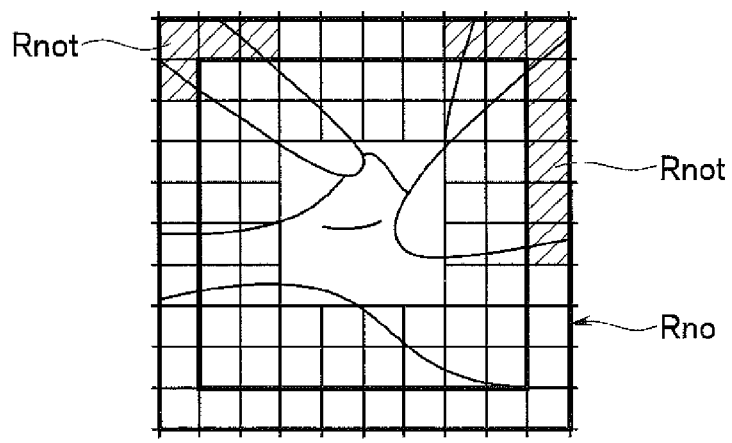
FIG. 6D is a view illustrating an outermost block region as a region in which a treatment instrument is present in an outermost region of the peripheral region.

Note that, as indicated by a thick frame in FIG. 6C, the innermost region Rni refers to a region (in the peripheral region Rn) which is connected in a square or rectangular shape (a closed belt-like region) that is adjacent to the square or rectangular central region Rc from the outside on the upper, lower, left and right sides thereof. Likewise, as indicated by a thick frame (in the peripheral region Rn) that is shown in FIG. 6D, the outermost region Rno refers to a region which is connected in a square or rectangular shape (a closed belt-like region) that is furthest away from the central region Rc.

As described above, the innermost block region arithmetic circuit 64a detects a number of regions Mi in which an image of the treatment instrument 17 is present among a total number of regions Ni forming the innermost region Rni, as the innermost block region Rnit, and also calculates a proportion Mi/Ni which represents the number of regions Mi in the total number of regions Ni.

Further, the outermost block region arithmetic circuit 64b detects a number of regions Mo in which an image of the treatment instrument 17 is present among a total number of regions No forming the outermost region Rno, as the outermost block region Rnot, and also calculates a proportion Mo/No which represents the number of regions Mo in the total number of regions No.

Note that, in the present embodiment, although a case is described in which the left and right images are displayed in a square or rectangular shape, the present invention can also be applied in substantially the same manner to a case in which the left and right images are displayed in a circular shape. In such a case, the central region Re is a circular region at a central part of each image, and the peripheral region Rn is an annular region on the outer side of the circular central region Rc. Furthermore, the innermost region Rni and the like can also be defined in a substantially similar manner (although the shape thereof will be different to the case of a square or rectangular shape).

Note that, although in FIG. 5 a configuration example is illustrated in which the innermost block region arithmetic circuit 64a and the outermost block region arithmetic circuit 64b are provided inside the treatment instrument region evaluation circuit 64, a configuration may also be adopted in which the aforementioned circuits 64a and 64b are provided outside the treatment instrument region evaluation circuit 64.

In the present embodiment, the control portion 56 controls operations of the image analysis processing circuit 52d and the image compositing portion 55. Under control of the control portion 56, the treatment instrument region evaluation circuit 64 inside the image analysis processing circuit 52d sets a blur region and a blur intensity in an image of the peripheral region Rn by causing blur data that corresponds to an analysis result data that is in accordance with a proportion that an image of the treatment instrument 17 occupies in the peripheral region Rn to be outputted from the reference DB 54. Further, in accordance with control of the control portion 56, the image compositing portion 55 uses the blur region and blur intensity that are set to execute blur processing on the left and right images, composites a 3D image based on the left and right images that were subjected to blur processing, and generates a 3D composite signal.

More specifically, the control portion 56 controls so as to set a blur region in accordance with the proportion Mi/Ni which represents the number of regions Mi forming the innermost block region Rnit in which an image of the treatment instrument 17 is present divided by (the total number of regions Ni of) the innermost region Rni according to an arithmetic operation result of the innermost block region arithmetic circuit 64a, to set a blur intensity in accordance with the proportion Mo/Ni which represents the number of regions Mo forming the outermost block region Rnot in which an image of the treatment instrument 17 is also present divided by (the total number of regions No of) the outermost region Rno according to an arithmetic operation result of the outermost block region arithmetic circuit 64b, and so that the image compositing portion 55 generates a 3D composite signal obtained by compositing a 3D image.

Further, as described later, the control portion 56 performs control to set a blur region so as to expand from the outermost region Rno to the innermost region Rni side as the proportion Mi/Ni increases, the Mi/Ni being a ratio of an image of the treatment instrument 17 occupying in the innermost region Rni, according to an arithmetic operation result of the innermost block region arithmetic circuit 64a, and so as to set a blur intensity in the blur region so as to increase in steps as the proportion Mo/No increases, the Mo/No being a ratio of the image of the treatment instrument 17 occupying in the outermost region Rno, according to an arithmetic operation result of the outermost block region arithmetic circuit 64b.

Note that, instead of the control portion 56 controlling operations of the treatment instrument region evaluation circuit 64 inside the image analysis processing circuit 52d from outside as described above, for example, a configuration may be adopted that includes a control function according to the control portion 56 inside the treatment instrument region evaluation circuit 64 and performs setting of a blur region and setting of a blur intensity using the control function, and not through the control portion 56 that is outside the treatment instrument region evaluation circuit 64. With respect to the reference DB 54 also, a configuration may be adopted so as to output blur data that corresponds to analysis result data which is obtained by the image analysis portion 52 to the image compositing portion 55, without the blur data passing through the external control portion 56. In other words, the present invention is not limited to a configuration as shown in FIG. 3 or FIG. 4 in which the control portion 56 is provided outside the image analysis portion 52, the reference DB 54 and the image compositing portion 55, and a configuration may also be adopted in which a part of the control function of the control portion 56 is provided inside the image analysis portion 52, inside the reference DB 54 or inside the image compositing portion 55. In the following description of operations, a case in which a configuration is adopted that is close to the latter configuration is mainly described.

The image processing portion 11 of the present embodiment constituting a stereoscopic endoscopic image processing apparatus includes: the synchronization adjustment portion 53 that is configured to perform a synchronization adjustment between a left-eye image signal that represents a left-eye image and a right-eye image signal that represents a right-eye image, based on output signals of the CCDs 27a and 27b as left and right image pickup devices that are provided in the 3D endoscope 4 as a stereoscopic endoscope; and the image analysis portion 52 that is configured to analyze a region that an image of the treatment instrument 17 occupies in the peripheral region Rn around the central region Re in an image of at least one image signal among the left-eye image signal and the right-eye image signal; in which the image analysis portion 52 has: the image dividing circuit 61 which forms an image dividing portion that segments the peripheral region Rn around the central region Re in the image that is obtained based on the image signal that is inputted, to thereby divide the peripheral region Rn into a predetermined number of regions; the color component analysis circuit 62 which forms a color component analysis portion that analyzes color components inside each of the predetermined number of regions; the image edge component extraction circuit 63 which forms an image edge component extraction portion that extracts an edge component of a straight component in each of the regions; the treatment instrument region evaluation circuit 64 which farms a treatment instrument region evaluation portion that evaluates a size of a region that an image of the treatment instrument 17 occupies in the peripheral region Rn based on an analysis result of the color component analysis portion and an extraction result of the image edge component extraction portion; the innermost block region arithmetic circuit 64a which forms an innermost block region arithmetic portion that detects, as an innermost block region Rnit, blocks of a number of regions Mi in which an image of the treatment instrument 17 is present in an innermost region Rni as a region on the innermost side on the peripheral region Rn based on an evaluation result of the treatment instrument region evaluation portion, and performs an arithmetic operation with respect to the innermost block region Rnit; and the outermost block region arithmetic circuit 64b which forms an outermost block region arithmetic portion that detects, as an outermost block region Rnot, blocks of a number of regions Mo in which an image of the treatment instrument 17 is present in an outermost region Rno as a region on the outermost side in the peripheral region Rn based on an evaluation result of the treatment instrument region evaluation portion, and performs an arithmetic operation with respect to the outermost block region Rnot; the image processing portion 11 further including: the reference DB 54 which forms a blur information generation portion that, in accordance with an analysis result of the image analysis portion 52, generates information regarding a blur region as a region in which to perform blur processing on the image in the peripheral region Rn, and information regarding a blur intensity at a time of performing blur processing on the image in the peripheral region Rn; and the image compositing portion 55 configured to composite and output a 3D image with respect to which blur processing is performed on each of the left-eye image and the right-eye image in accordance with a synchronization adjustment result of the synchronization adjustment portion 53 and a generation result of the blur information generation portion.

Next, operations of the present embodiment will be described. FIG. 7 illustrates typical processing procedures in a case of performing operations of the present embodiment.

When the power of the stereoscopic endoscope apparatus 1 that is used in the present embodiment is turned on and operation of the stereoscopic endoscope apparatus 1 starts, first, in step S1, as initial settings, a user such as a doctor sets the central region Re and the peripheral region Rn in, for example, a left image as one image, and also sets the number of divisions (or predetermined number) N into which to divide the peripheral region Rn into small regions Rb (see FIG. 6A). Note that, in a case where the central region Re, the peripheral region Rn and the number of divisions N were already set when the stereoscopic endoscope apparatus 1 was used in the past, such as at the previous time of use, the settings data for those settings may be used. Further, although there is no necessity to set the central region Re, the peripheral region Rn and the regions Rb and the like with respect to a right image, in the case of performing blur processing, the central region Re, the peripheral region Rn and the regions Rb that are set for the left image are applied to the right image also.

Next, in step S2, the doctor performs a stereoscopic observation using the 3D endoscope 4. Signals of left and right image pickup images that are picked up by the left and right image pickup devices of the 3D endoscope 4 are converted to left and right 2D image signals by the processors 7A and 7B, and the left and right 2D image signals are converted into a 3D image signal by the 3D mixer 8 and then inputted to the image processing portion 11 of the 3D monitor 9. With respect to the 3D image signal that is inputted to the image processing portion 11, the changeover switch 51 is changed over for each field period by a changeover signal of the changeover signal generation circuit 53b.

Further, for example, a left image signal of an odd-numbered field period is inputted to the image analysis portion 52. The left image signal that is inputted to the image analysis portion 52 is temporarily stored in the memory 52c. The image analysis processing circuit 52d then performs analysis as described hereunder with respect to the left image signal that is stored in the memory 52c. Note that, although in the present embodiment a case is described in which a left image signal is inputted to the image analysis portion 52, a configuration may also be adopted in which a right image signal is inputted to the image analysis portion 52 instead of the left image signal. In such a case, the left image signal may be stored in the memory 53d.

As shown in step S3, with respect to the image of the left image signal, the image dividing circuit 61 of the image analysis processing circuit 52d divides the peripheral region Rn around the central region Re into the above described number of divisions N, as shown in FIG. 6A. The following processing is performed with respect to each region Rb into which the peripheral region Rn is divided.

In the subsequent step S4, the color component analysis circuit 62 of the image analysis processing circuit 52d performs processing to subject an image of an image signal of each region Rb in the peripheral region Rn to color analysis into color components. FIG. 6B illustrates a state in which color analysis is being performed with respect to a single region Rb that is indicated by diagonal lines.

The color of a treatment instrument such as the treatment instrument 17 is normally set to silver or grey so as to easily distinguish the treatment instrument from a color tone of a living organism. Therefore, the color component analysis circuit 62 performs color analysis processing so as to extract a silver or grey color component, that is, a specific color component of the treatment instrument 17. Note that, in FIG. 6B, an image is illustrated in which, for example, surgery is performed using three treatment instruments 17a, 17b and 17c as the treatment instrument 17.

Next, in step S5, the image edge component extraction circuit 63 of the image analysis processing circuit 52d performs processing to extract straight (or linear) edge components with respect to an image of an image signal of the respective regions Rb in the peripheral region Rn. Since a proportion that a linear rod portion occupies in a treatment instrument such as the treatment instrument 17 is large, the image edge component extraction circuit 63 extracts edge components that extend rectilinearly. In FIG. 6B, a state is illustrated in which edge components Ea, Eb and Ec of rod portions that extend rectilinearly are extracted. Although the image edge component extraction circuit 63 focuses on extracting edge components that extend rectilinearly, a configuration may also be adopted in which rounded edge components are also extracted.

In the subsequent step S5, the treatment instrument region evaluation circuit 64 of the image analysis processing circuit 52d evaluates (or identifies) the size that the image of the treatment instrument 17 occupies in the peripheral region Rn based on the analysis result (specific color component extraction result) of the color component analysis circuit 62 and the result of extraction of straight edge components (or edge components in straight components) by the image edge component extraction circuit 63. Specifically, the treatment instrument region evaluation circuit 64 evaluates (or identifies) the size that the image of the treatment instrument 17 occupies in the peripheral region Rn based on the regions Rb that are enclosed by the edge components Ea, Eb and Be in the peripheral region Rn in FIG. 6B.

Next, in step S6, the innermost block region arithmetic circuit 64a detects blocks of a treatment instrument region in which (an image of) the treatment instrument 17 is present in the innermost region Rni, illustrated in FIG. 6C, as the innermost block region Rnit. Further, the innermost block region arithmetic circuit 64a calculates a proportion Mi/Ni which represents (the number of regions forming) the innermost block region Rnit occupying in the innermost region Rni. In the example illustrated in FIG. 6C, in the innermost region Rni, since the total number of the regions Rb is 20 and the total number of the innermost block regions Rnit is 7, the proportion of the innermost block region Rnit occupying is 7/20.

Next, in step S7, the outermost block region arithmetic circuit 64b detects blocks of a treatment instrument region in which (an image of) the treatment instrument 17 is present in the outermost region Rno, illustrated in FIG. 6D, as the outermost block region Rnot. In the example illustrated in FIG. 6D, in the outermost region Rno, since the total number of the regions Rb is 36 and the total number of (the number of regions forming) the outermost block regions Rnot is 12, a proportion Mo/Noof the innermost block region Rnit occupying is 12/36 (=1/3).

The treatment instrument region evaluation circuit 64 then sends analysis result data including the result showing the proportion Mi/Ni of the innermost block region Rnit occupying as the arithmetic operation result of the innermost block region arithmetic circuit 64a, and the result showing the proportion Mo/No of the outermost block region Rnot occupying as the arithmetic operation result of the outermost block region arithmetic circuit 64b to the reference DB 54.

Next, in step S8, the reference DB 54 generates information regarding a blur region that is in accordance with the data for the result showing the proportion that the innermost block region Rnit occupies, and outputs the information to the image compositing portion 55. The processing to set a blur region is described later referring to FIG. 8A and FIG. 8B.

Further, next, in step S9, the reference DB 54 generates information regarding a blur intensity that is in accordance with the data for the result showing the proportion Mo/No of the outermost block region Rnot occupying, and outputs the information to the image compositing portion 55. The processing to set a blur intensity is described later referring to FIG. 9A and FIG. 9B.

Thereafter, in step S10, in the image compositing portion 55, taking blur data that includes the information regarding a blur intensity and a blur region from the reference DB 54 as parameters for performing blur processing, the blur filter circuit 55a performs blur processing with respect to each of left and right images of odd-numbered and even-numbered fields constituting the same frame that are read out from the memory 52c and the memory 53d, and the resulting images are combined by the superimposing circuit 55b to generate a 3D composite image.

A 3D composite image signal as an image signal of the 3D composite image that is generated is outputted to the display portion 43 so that the left and right images are displayed in a state in which polarization directions are orthogonal on the display screens of the display portion 43. The doctor D stereoscopically views the 3D composite image by putting on the 3D glasses 10 and observing the displayed 3D composite image. Note that, after the processing in step S10, the operation returns to the processing in step S4 to repeat the same processing for each frame in the moving image.

Figure 10:
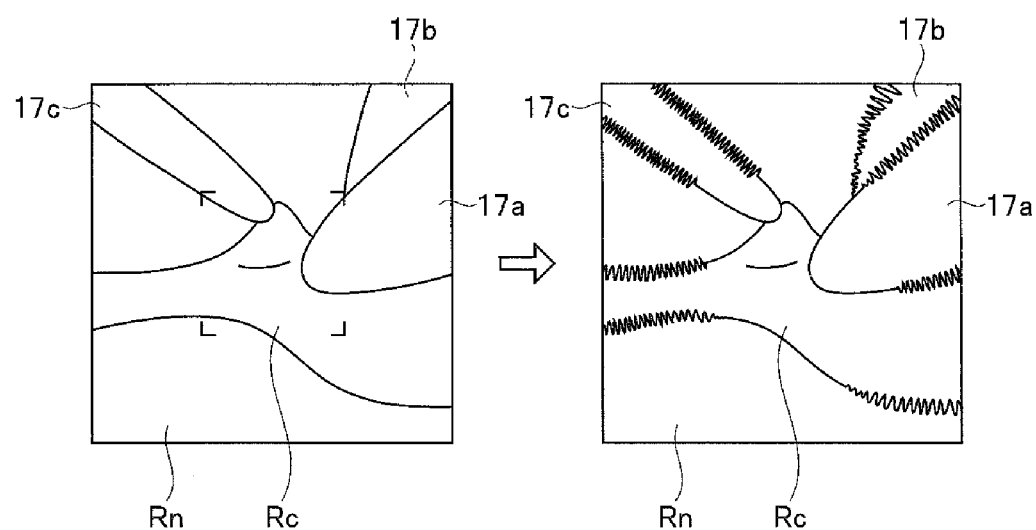
FIG. 10 is a view illustrating an image prior to blurring, and an image after undergoing blur processing.

FIG. 10 illustrates an example of an image before and after performing blur processing in the above described manner. An image on the left side in FIG. 10 shows, for example, a left image before performing blur processing, and the left image after blur processing is shown on the right side in FIG. 10. On the left side in FIG. 10, four corners that serve as a boundary between the central region Re and the peripheral region Rn are illustrated in a small form. Image processing is performed so that the edge portions of images of the treatment instruments in the peripheral region Rn are blurred. In practice, portions other than edge portions are also subjected to blur processing. Note that a right image of the same frame as the left image is also subjected to blur processing in the same manner as the left image (see FIG. 12).

Images of the treatment instruments 17 in the central region Re shown on the right side in FIG. 10 are clearly displayed in a state in which blur processing is not performed thereon, while on the outer side of the central region Re, the images of the treatment instruments 17 have been subjected to blur processing in accordance with the proportions that the respective images of the treatment instruments 17 occupy in the overall image. Because the rod portions of the treatment instruments 17 within the peripheral region Rn become blurred as a result of the blur processing, when the images of the treatment instruments 17 in the peripheral region Rn are viewed during stereoscopic observation, a factor that decreases the visual characteristics of the stereoscopic observation, specifically, a visual characteristic that imparts an uncomfortable feeling such as a feeling that a treatment instrument will protrude out to the front side can be suppressed or reduced. Accordingly, it is possible for the doctor to perform treatment while stereoscopically viewing the relevant site in a state in which a factor that causes the doctor to experience an uncomfortable feeling is suppressed or reduced.

Figure 8A:
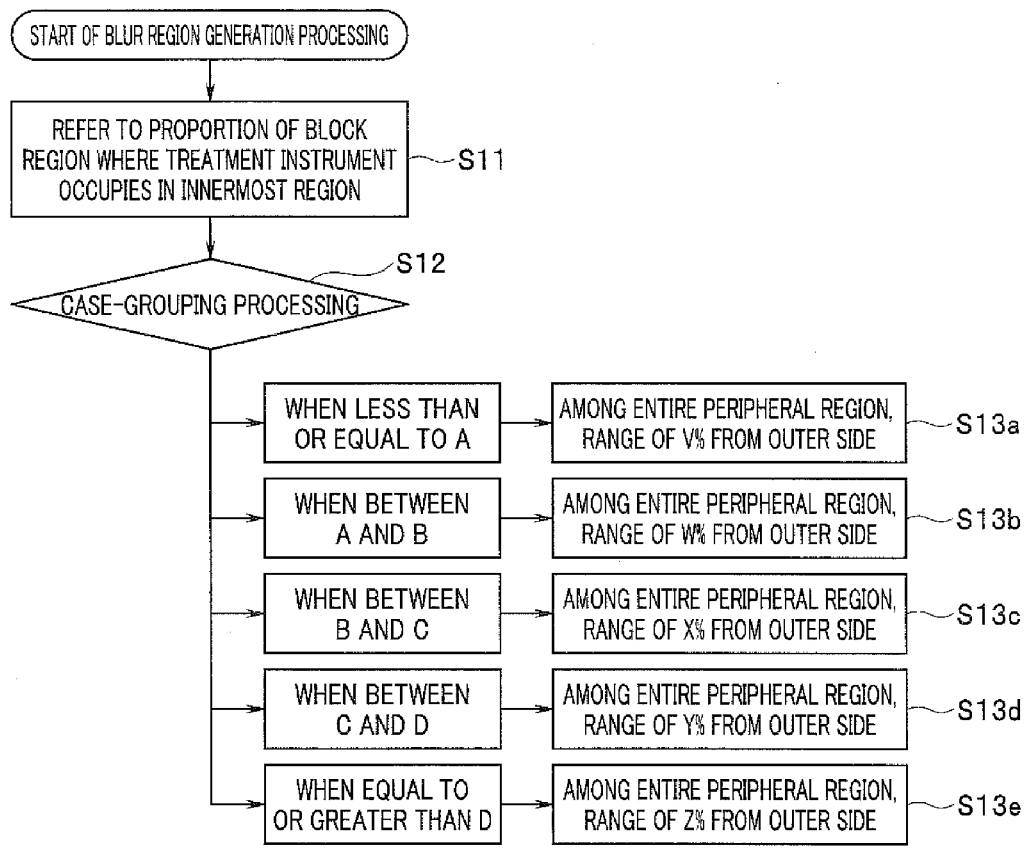
FIG. 8A is a flowchart illustrating processing procedures for generating or setting a blur region.

FIG. 8A illustrates processing in which the reference DB 54 generates (sets) a blur region in accordance with a proportion that the innermost block region Rnit occupies that is obtained as an arithmetic operation result of the innermost block region arithmetic circuit 64a.

As shown in step S11, the reference DB 54 refers to a proportion of the innermost block region Rnit occupying in an image of the treatment instrument 17, more specifically, a rod block region of a rod portion of the image of the treatment instrument 17, in the innermost region Rni. Next, as shown in step S12, under control of the control portion 56, the reference DB 54 performs the following case-grouping processing in accordance with the result of referring to the proportion. Note that a configuration may also be adopted in which the control portion 56 performs the following processing.

For example, in a case where the proportion is less than or equal to A, as shown in step S13a, among the entire peripheral region Rn, the reference DB 54 sets a range of V % from the outer side as a blur region;

in a case where the proportion is between A and B, as shown in step S13b, among the entire peripheral region Rn, the reference DB 54 sets a range of W % from the outer side as a blur region;

in a case where the proportion is between B and C, as shown in step S13c, among the entire peripheral region Rn, the reference DB 54 sets a range of X % from the outer side as a blur region;

in a case where the proportion is between C and D, as shown in step S13d, among the entire peripheral region Rn, the reference DB 54 sets a range of Y % from the outer side as a blur region; and in a case where the proportion is equal to or greater than D, as shown in step S13e, the reference DB 54 sets a range of Z % from the outer side as a blur region.

Figure 8B:
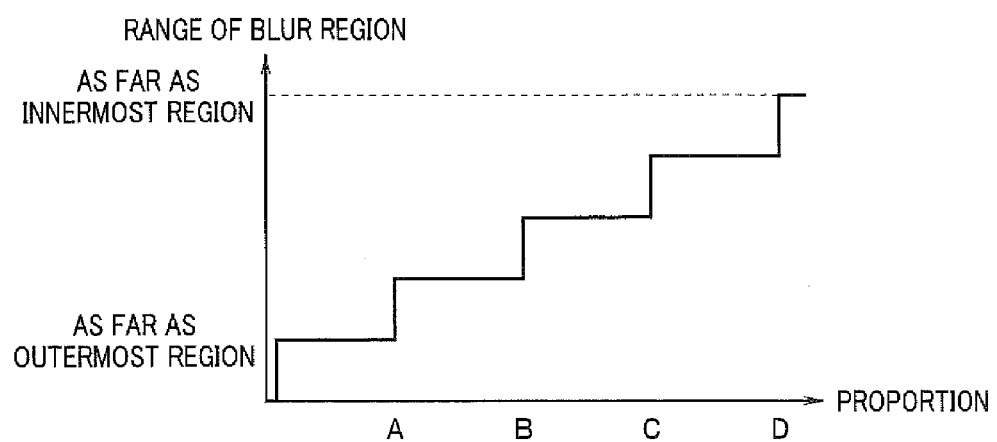
FIG. 8B is a view illustrating ranges of a blur region that are set in accordance with a proportion of an innermost block region by processing in FIG. 8A.

FIG. 8B illustrates an example of proportions of the innermost block region Rnit and ranges of the blur region that correspond to FIG. 8A. As the proportion of the innermost block region Rnit increases, the range of the blur region increases stepwise from the outermost region Rno side to the innermost region Rni side. Note that, in a case where the proportion of the innermost block region Rnit is 0, the range of the blur region is also 0.

Figure 9A:
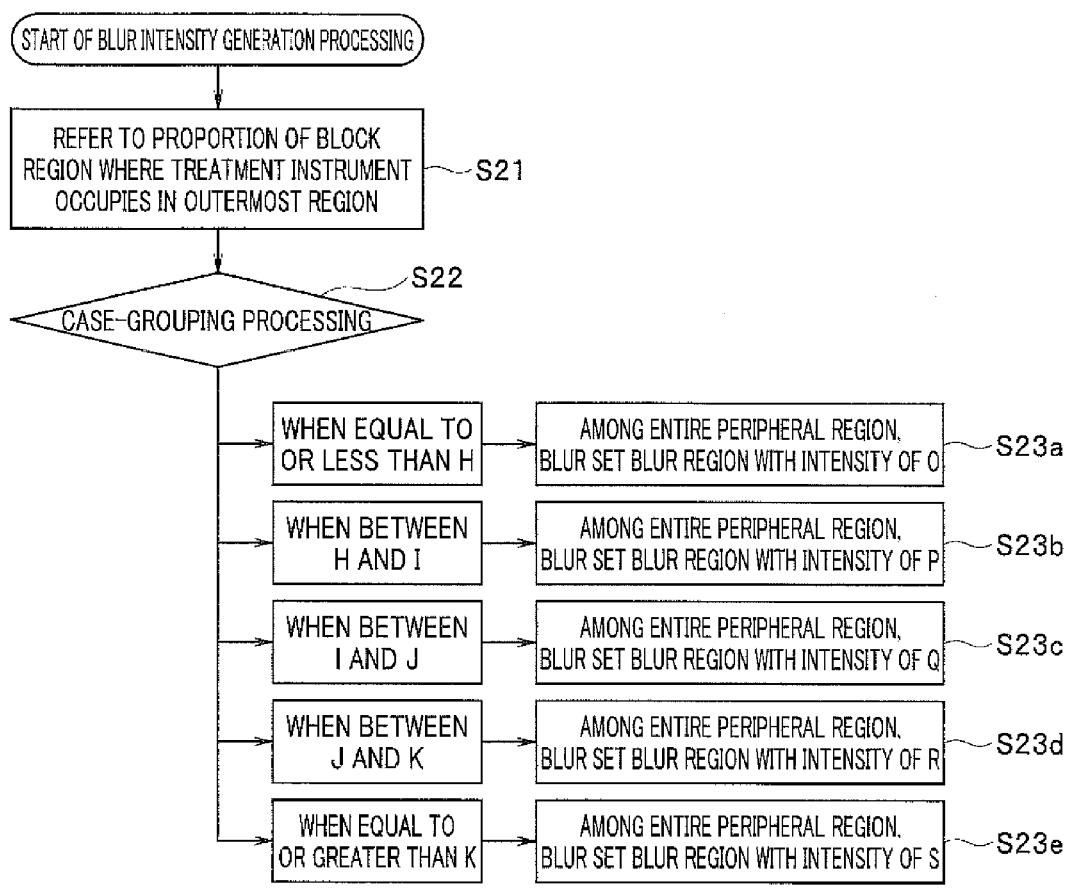
FIG. 9A is a flowchart illustrating processing procedures for generating or setting a blur intensity.

FIG. 9A illustrates processing in which the reference DB 54 generates (sets) a blur intensity in accordance with a proportion of the outermost block region Rnot occupying, which is obtained as an arithmetic operation result of the outermost block region arithmetic circuit 64b.

As shown in step S21, the reference DB 54 refers to a proportion of the outermost block region Rnot occupying in an image of the treatment instrument 17, more specifically, a rod block region of a rod portion of the image of the treatment instrument 17, in the outermost region Rno. Next, as shown in step S22, under control of the control portion 56, the reference DB 54 performs the following case-grouping processing in accordance with the result of referring to the proportion. Note that a configuration may also be adopted in which the control portion 56 performs the following processing.

For example, in a case where the proportion is equal to or less than H, as shown in step S23a, among the entire peripheral region Rn, the reference DB 54 blurs the set blur region with an intensity of O.

In a case where the proportion is between H and I, as shown in step S23b, among the entire peripheral region Rn, the reference DB 54 blurs the set blur region with an intensity of P.

In a case where the proportion is between I and J, as shown in step S23c, among the entire peripheral region Rn, the reference DB 54 blurs the set blur region with an intensity of Q.

In a case where the proportion is between J and K, as shown in step S23d, among the entire peripheral region Rn, the reference DB 54 blurs the set blur region with an intensity of R.

In a case where the proportion is equal to or greater than K, as shown in step S23e, among the entire peripheral region Rn, the reference DB 54 blurs the set blur region with an intensity of S.

Figure 9B:
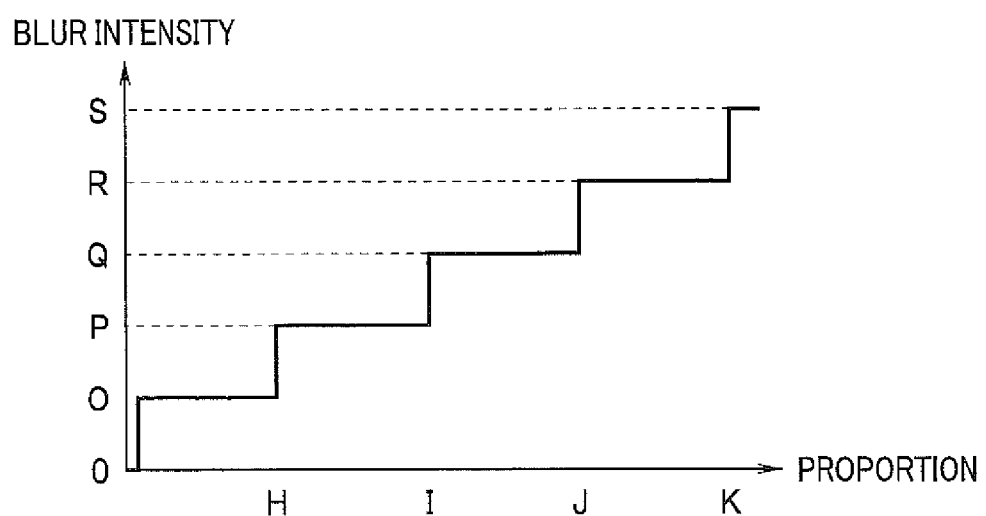
FIG. 9B is a view illustrating blur intensities that are set in accordance with a proportion of an outermost block region by processing in FIG. 9A.

FIG. 9B illustrates an example of proportions of the outermost block region Rnot and bluffing intensities that correspond to FIG. 9A. As the proportion of the outermost block region Rnot increases, the blur intensity increases stepwise. Note that, in a case where the proportion of the outermost block region Rnot is 0, the blur intensity is also 0.

Figure 11A:
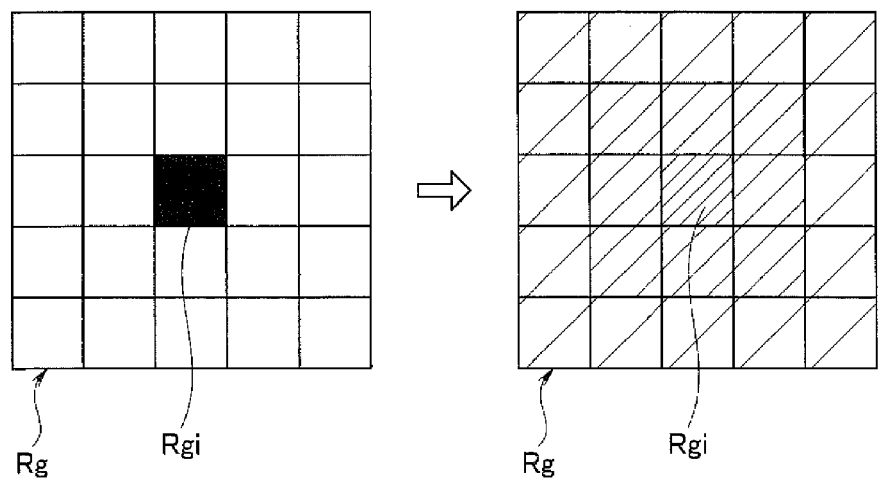
FIG. 11A is an explanatory drawing for describing a case of performing blur processing with respect to a blur region.

FIG. 11A is a view for describing a case of performing blur processing with respect to a blur region that is set in accordance with a proportion of the innermost block region Rnit. By causing color information of, for example, a blurring target pixel Rgi shown in black that is included in a blur region Rg shown on the left side of FIG. 11A to gradually extend to pixels around the blurring target pixel Rgi also, as shown on the right side in FIG. 11A, blur processing is performed so as to cause the color information of the blurring target pixel Rgi to spread to the surrounding pixels also.

Figure 11B:
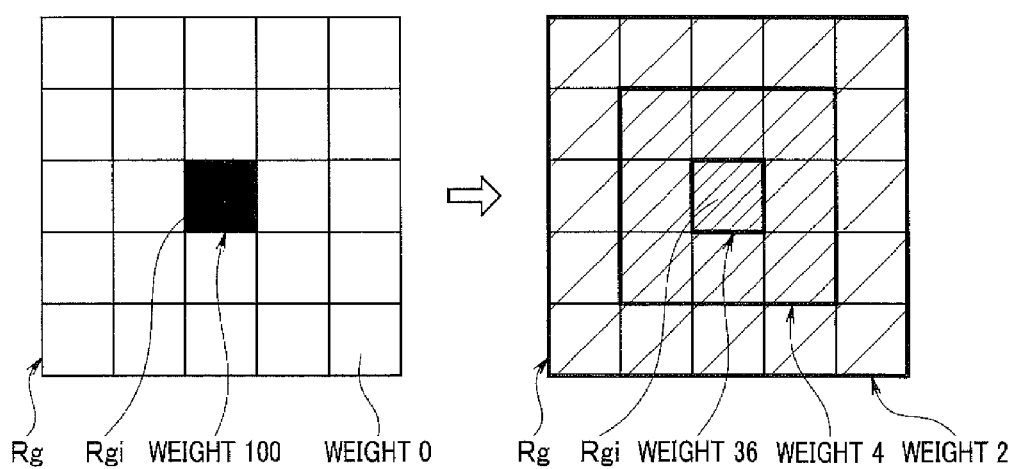
FIG. 11B is an explanatory drawing for describing a case of performing blur processing using the numerical example in FIG. 11A.

A specific example will now be described. In a case where, as illustrated in FIG. 11B, a weight (pixel value) of color information of the blurring target pixel Rgi prior to performing blur processing is taken as 100 and a weight (pixel value) of the pixels around the blurring target pixel Rgi is taken as 0, the weight (weighting factor) of color information of the blurring target pixel Rgi is set to 36, the weight of color information of eight pixels as first peripheral pixels that are nearest to the periphery of the blurring target pixel Rgi is set to 4, and the weight of color information of 16 pixels as second peripheral pixels that are at positions around the first peripheral pixels is set to 2 by the blur processing. Thus, blur processing is performed so as to maintain the weight (100) of the color information of the blurring target pixel Rgi after blur processing at the same value as before the blur processing, and to spread the weight of the color information to the peripheral pixels.

In this manner, all pixels within the blur region Rg are set as the blurring target pixel Rgi, and blur processing is perform.

Note that, in the case of changing the blur intensity, a configuration may be adopted that changes the combination of values of the weights 36, 4 and 2, or adds an image before blur processing and an image after blur processing to perform blur processing, and changes the blur intensity by changing a proportion in the case of adding the two images. For example, in the former case of changing the weighted combination of values, when changing from the combination of values of weights 36, 4 and 2 to, for example, a combination of values of weights 20, 4 and 3, a combination of values of weights 12, 4 and 3.5, or weights 4, 4 and 4, the blur intensity (or blurring intensity, or degree of blurring) sequentially increases. In the case of changing the blur intensity by means of a combination of values of weights in this manner, as the proportion of the outermost block region Rnot (image of the treatment instrument 17) occupying as input data of an analysis result increases, as described above, the reference DB 54 outputs the data in which the combination of weight values is changed to the blur filter circuit 55a as blur data.

Further, a low-pass filter may also be used for blur processing. At such time, a configuration may be adopted so as to increase the blur intensity (or degree of blurring) by lowering the cut-off frequency of the low-pass filter as the blur intensity is increased. In this case; as the proportion of the outermost block region Rnot (image of the treatment instrument 17) occupying as input data of an analysis result increases, the reference DB 54 outputs data in which the aforementioned cut-off frequency of the low-pass filter is lowered as blur data to the blur filter circuit 55a.

Figure 12:
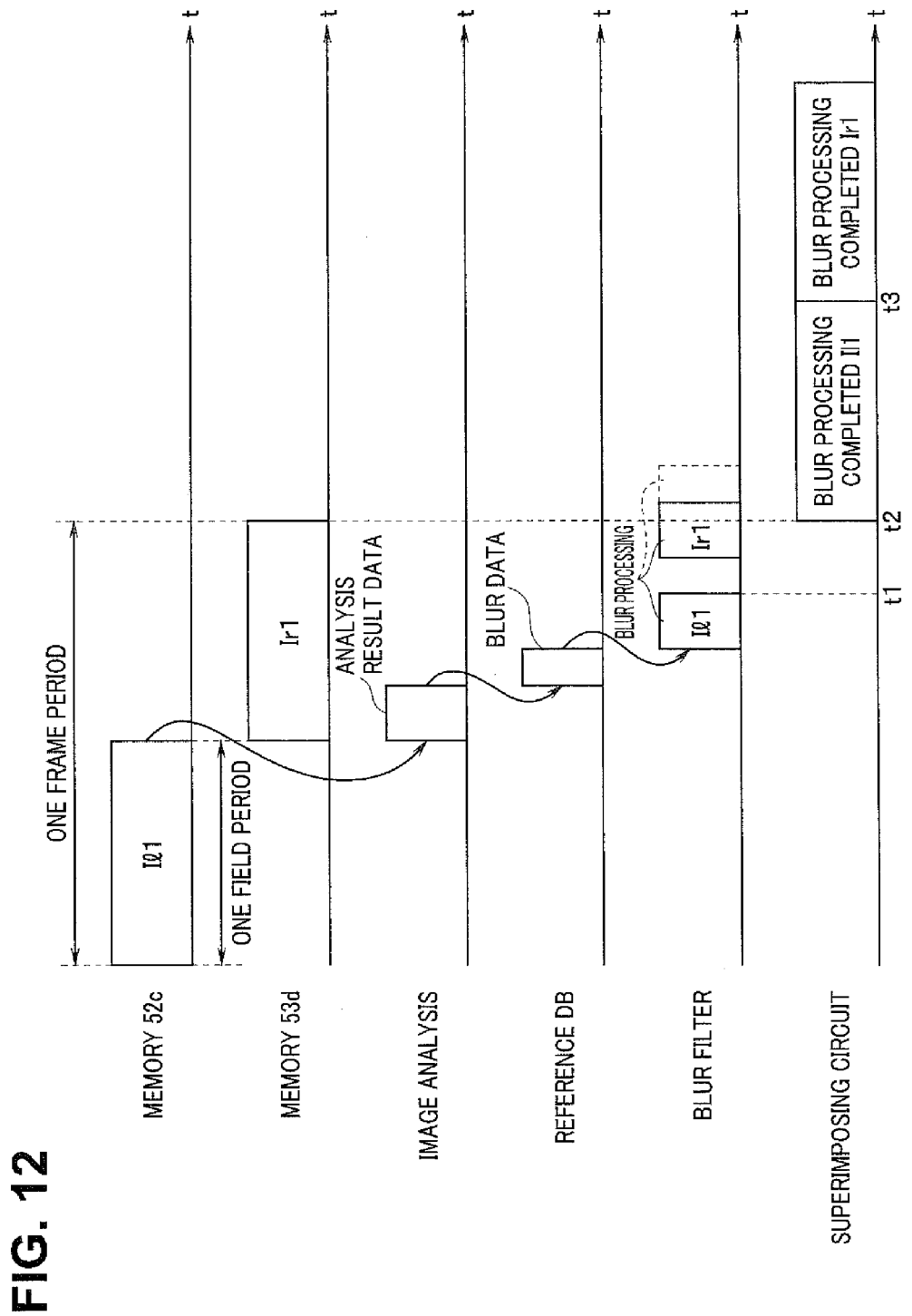
FIG. 12 is a timing chart of operations of the first embodiment.

FIG. 12 illustrates a schematic timing chart for a case of generating a 3D composite image in the present embodiment.

For a 3D image of a 3D image signal that is inputted to the image processing portion 11, a left image Il1 and a right image Ir1 that constitute an initial (first) single frame image are written into the memory 52c and the memory 53d, respectively, via the changeover switch 51 that is changed over for each single field period (in a case of displaying a 3D image of a single frame). Here, numeral "1" in the reference character "Il1" or "Ir1" indicates that the relevant image is an image of a first frame. During a single field period in which the right image hi is written into the memory 53d, the image analysis processing circuit 52d performs image analysis on the left image Il1 that is written in the memory 52c, generates analysis result data, and outputs the analysis result data to the reference DB 54. The reference DB 54 outputs blur data corresponding to the analysis result data to the blur filter circuit 55a of the image compositing portion 55.

The blur filter circuit 55a of the image compositing portion 55 uses the blur data to perform blur processing with respect to the left image Il1 in the memory 52c, and after the blur processing with respect to the left image Il1 is ended, the blur filter circuit 55a stores the resulting left image Il1 in the memory 55c inside the superimposing circuit 55b. Note that the memory 55c has a memory capacity that stores an amount of data corresponding to a single frame for the left and right images Il1 and Ir1 that have been subjected to blur processing, respectively.

Further, at a timing after a time period (including a margin) that is required to complete blur processing with respect to the left image Il1, the memory controller 53c of the synchronization adjustment portion 53 reads out the right image Ir1 from the memory 53d, and performs a synchronization adjustment (or timing adjustment) so as to output the right image Ir1 to the blur filter circuit 55a. The blur filter circuit 55a performs blur processing in the same manner with respect to the right image Ir1 that is outputted from the memory 53d also, and stores the resulting image data in the memory 55c inside the superimposing circuit 55b.

As shown in FIG. 12, even if the blur filter circuit 55a starts blur processing with respect to the right image Ir1 immediately at a time t1 after blur processing with respect to the left image Il1 ends, the timing at which the blur processing ends will be at or after a time t2 that is a timing at which input of the right image Ir1 for a single frame ends. Therefore, for example, a configuration may also be adopted in which the blur filter circuit 55a performs blur processing with respect to the right image Ir1 at a time that is between the time t1 and the time t2. Note that a case where blur processing is performed with respect to the right image Ir1 at the time t2 is indicated by a dashed line in FIG. 12.

In the next single frame period (the starting time thereof is t2), the superimposing circuit 55b sequentially reads out, in the respective single field periods, the left image (that is, the left image for which blur processing is completed) Il1 and the right image (that is, the right image for which blur processing is completed) Ir1 that were subjected to blur processing, and outputs the resultant signal as a 3D image signal that was subjected to blur processing.

In FIG. 12, even if blur processing of the right image Ir1 is not completed at the time t2 at which the superimposing circuit 55b starts to output the left image Il1 that was subjected to blur processing, blur processing for the right image Ir1 is completed by a time t3 that is after one field period in which output of the left image Il1 ends (therefore, output of the 3D image signal is not hindered). Consequently, the synchronization adjustment portion may be configured so as to perform a synchronization adjustment or a timing adjustment so that blur processing with respect to the right image Ir1 can be completed (the right image Ir1 is inputted to the blur filter circuit 55a) by a time at which the superimposing circuit 55b finishes outputting a single corresponding to the amount of one frame of the left image Il1 that was subjected to blur processing (the time t3 in FIG. 12).

Note that, in the example in FIG. 12, when the next single frame period begins, a left image Il2 is written in the memory 52c in the initial single field period in the next frame and a right image Ir2 is written in the memory 53d in the next field period, and similar processing is repeated. By performing the image processing as illustrated in FIG. 12, a 3D image signal that has undergone blur processing can be generated and outputted with a delay of only a single frame period.

Therefore, the synchronization adjustment portion in the present embodiment forms (a function of) a frame synchronization adjustment circuit that has a memory (53d in FIG. 4) that temporarily stores an image of the other image signal belonging to the same frame as an image of one image signal with respect to which analysis of a region which an image of the treatment instrument 17 occupies is performed by the image analysis portion 52, and that performs a synchronization adjustment so that a 3D image signal that was subjected to blur processing by the blur filter circuit 55a that forms a blur processing portion with respect to an image of the one image signal and an image of the other image signal is outputted after a single frame period from the frame in which the one image signal is inputted.

Further, the synchronization adjustment portion 53 may be configured to have a memory (for example, the memory 53d) that temporarily stores the other image belonging to the same frame as an image of one image signal with respect to which analysis of a region which an image of the treatment instrument 17 occupies is performed by the image analysis portion 52, and to perform synchronization adjustment so that, after blur processing is performed with respect to the one image signal upon receiving a signal after the start of analysis with respect to an image of the one image signal by the image analysis portion 52 or after the analysis result, the other image is outputted to the image compositing portion 55 so as to start blur processing with respect to the image of the other image signal at a time that the one image for a 3D image that was subjected to blur processing is outputted in the next frame period.

The image compositing portion 55 subjects the left and right image signals that underwent blur processing by the blur filter circuit 55a to a synchronization adjustment (or a timing adjustment) using the memory 53c, and sequentially outputs the left and right image signals that underwent blur processing, in adjacent fields. In this case, the synchronization adjustment portion 53 and the memory 53c perform a synchronization adjustment so that the left and right image signals that underwent blur processing are outputted after a single frame period from each frame in which the left and right image signals are inputted to the image processing portion 11.

According to the present embodiment that operates in this manner, by blurring at least an image of a treatment instrument in the peripheral region Rn while maintaining a state in which stereoscopical vision is enabled in a state of a clear image at the central region Rc in a 3D image that is displayed on the display screen of the 3D monitor 9, the cause of an uncomfortable feeling or the like that is due to a treatment instrument can be decreased. Thus, according to the present embodiment, while maintaining the perceptual characteristics of stereoscopic observation, a decrease in the perceptual characteristics of the stereoscopic observation that is caused by a treatment instrument can be suppressed or reduced.

Further, since a configuration is adopted so as to set a blur region in which to perform blur processing as well as a blur intensity in accordance with a proportion of a region in which a treatment instrument is detected with respect to a detection region in which a detection is performed to determine whether or not an image of a treatment instrument is present within a peripheral region Rn, an appropriate image of the peripheral region Rn that takes into consideration the proportion occupied by an image of a treatment instrument in the peripheral region Rn can be provided.

Figure 13:
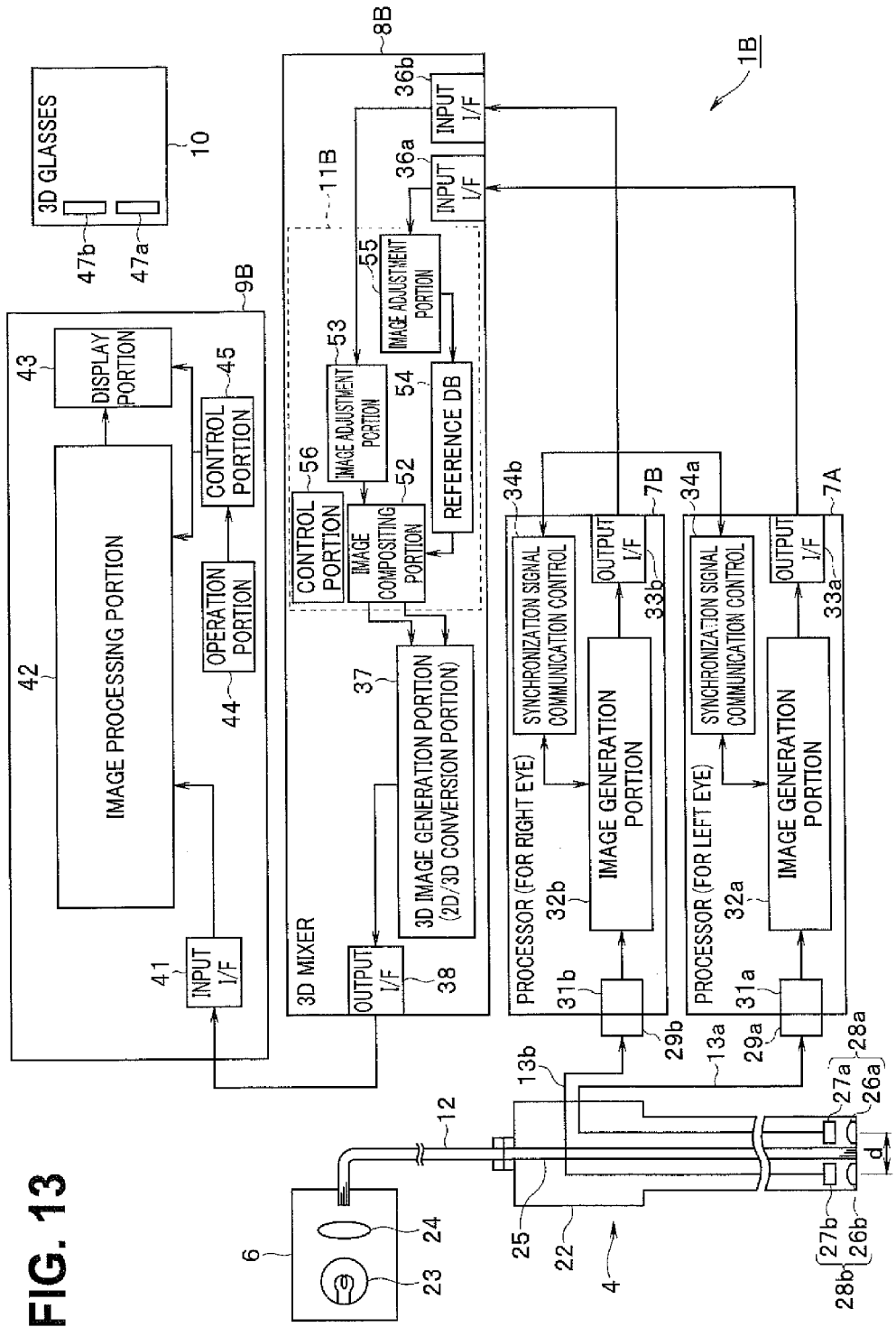
FIG. 13 is a view illustrating the internal configuration of a stereoscopic endoscope apparatus equipped with a modification of the first embodiment.

Note that, although in the first embodiment an example is described in which the image processing portion 11 constituting a stereoscopic endoscopic image processing apparatus is provided inside the 3D monitor 9, for example, a configuration may also be adopted in which an image processing portion 11B constituting a stereoscopic endoscopic image processing apparatus is provided inside the 3D mixer 8, as in the modification illustrated in FIG. 13.

A stereoscopic endoscope apparatus 1B illustrated in FIG. 13 has a configuration in which, relative to the stereoscopic endoscope apparatus 1 illustrated in FIG. 1, the 3D mixer 8 is changed to a 3D mixer 8B, and a 3D monitor 9 is changed to a 3D monitor 9B.

Instead of the image processing portion 11 shown in FIG. 1, the 3D monitor 9B has an image processing portion 42 that performs image processing that displays an inputted 3D image signal on the display portion 43. The 3D monitor 9B in this case has a similar configuration to that of a known 3D monitor.

The 3D mixer 8B shown in FIG. 13 has a configuration in which, relative to the 3D mixer 8 shown in FIG. 1, an image processing portion 11B that performs blur processing is provided between the image input interfaces 36a and 36b and the 3D image generation portion 37.

Although fundamentally the image processing portion 11B has substantially the same functions as the above described image processing portion 11, while in the above described example the 3D image signal is inputted to the image processing portion 11, in the case of the configuration shown in FIG. 13, left and right 2D image signals are simultaneously inputted in parallel.

Consequently, in the image processing portion 11B shown in FIG. 13, the changeover switch 51 that is required in the configuration of the image processing portion 11, as well as a circuit for changing over the changeover switch 51 are not required. Accordingly, the image processing portion 11B includes the image analysis portion 52, the synchronization adjustment portion 53, the reference DB 54, the image compositing portion 55 and the control portion 56.

Note that, although the timings for the two images differ somewhat from the above described timings because the left and right image signals are simultaneously inputted, the operations to perform blur processing are the same as in the above described case. The left and right images that are simultaneously inputted are written to the memories 52c and 53d, respectively. Further, image analysis that is similar to the above described case is performed with respect to, for example, the left image as one image, analysis result data is generated, the reference DB 54 outputs blur data corresponding to the analysis result data to the image compositing portion 55, and the image compositing portion 55 performs blur processing on the left and right images, and simultaneously outputs left and right image signals that underwent blur processing to the 3D image generation portion 37.

The 3D image generation portion 37 combines the left and right image signals that underwent blur processing to generate a 3D image signal that underwent blur processing, and outputs the 3D image signal to the 3D monitor 9B. The 3D monitor 9B displays the inputted 3D image signal that underwent blur processing on the display portion 43, and the doctor D can put on the 3D glasses 10 and stereoscopically view the image on the display portion 43. Although the timing of image processing in the present modification is somewhat different from the above described first embodiment, the present modification has almost the same advantageous effects as in the first embodiment.

Note that, although in the foregoing first embodiment and modification a configuration is described in which a blur region is set in accordance with a proportion of the innermost block region Rnit (Mi/Ni when expressed as a proportion of a number of regions in the region Rb), and a blur intensity in the blur region is set in accordance with a proportion of the outermost block region Rnot (Mo/No when expressed as a proportion of a number of regions), a configuration may also be adopted in which a blur region is set in accordance with the proportion Mo/No of the outermost block region Rnot and a blur intensity in the blur region is set in accordance with the proportion Mi/Ni of the innermost block region Rnit.

Further, in the foregoing description, when the reference DB 54 outputs blur data that is based on analysis result data to (the blur filter circuit 55a of) the image compositing portion 55 and a state is entered in which blur processing is possible, the image analysis portion 52 outputs a left image signal that is read out from the memory 52c to (the blur filter circuit 55a of) the image compositing portion 55, and at a time that blur processing ends that is the same timing as reading out ends, the image analysis portion 52 notifies the end of blur processing with respect to the left image signal to (the memory controller 53c of) the synchronization adjustment portion 53. Further, the blur filter circuit 55a subsequently performs blur processing on a right image signal belonging to the same frame. However, the present invention is not limited to such procedures.

For example, a configuration may also be adopted in which, at a timing at which analysis result data is generated, the image analysis portion 52 sends a signal notifying the timing at which the analysis result data is generated to (the memory controller 53c of) the synchronization adjustment portion 53, and (the memory controller 53c of) the synchronization adjustment portion 53 performs a synchronization adjustment so that, after waiting for a time period in which a left image signal is read out from the memory 52c and blur processing by (the blur filter circuit 55a of) the image compositing portion 55 ends, a right image signal belonging to the same frame is outputted to (the blur filter circuit 55a of) the image compositing portion 55. In this case, the synchronization adjustment portion 53 adjusts so that, in substantially the same manner as in the above described case, one image that becomes one image signal and the other image that becomes the other image signal are outputted to the image compositing portion 55 at timings that are before and after each other.

Furthermore, as the blur filter circuit 55a shown in FIG. 4, a configuration may be adopted which is equipped with two blur filter circuits so as to perform blur processing on the left and right images at the same timing. In this case, a configuration may be adopted so that the memory controllers 52b and 53c read out left and right image signals from the memories 52c and 53d respectively in synchronization with each other, and blur processing by the two blur filter circuits is performed in parallel. In this case, the synchronization adjustment portion 53 adjusts so that one image that becomes one image signal and the other image that becomes the other image signal are outputted to the image compositing portion 55 at synchronized timings.

Note that a configuration may also be adopted in which a blur region and a blur intensity is set differently to the above described manner of setting a blur region.

For example, a configuration may be adopted in which, with respect to the peripheral region Rn shown in FIG. 6B, a region in which images of the treatment instruments 17a, 17b and 17c are present in the peripheral region Rn that are determined based on a result of analysis of color components and a result of extracting edge components is taken as a candidate region in which to perform blur processing, a blur region is then set from an outermost circumference side of the candidate region in accordance with a proportion of the innermost block region Rnit (see FIG. 6C) in the innermost region Rni, and a blur intensity in the blur region is set in accordance with a proportion of the outermost block region Rnot (see FIG. 6D) in the outermost region Rno.

Further, the above described image analysis portion 52, synchronization adjustment portion 53, and image compositing portion 55 may be formed using electronic circuit elements, or may be formed by means of software using a central processing unit (CPU).

What is claimed is:

1. A stereoscopic endoscopic image processing apparatus, comprising: at least one processor programmed to execute: a synchronization adjustment portion configured to perform a synchronization adjustment between a left-eye image signal that represents a left-eye image and a right-eye image signal that represents a right-eye image, based on output signals of left and right image pickup devices provided in a stereoscopic endoscope; an image analysis portion configured to analyze a region that an image of a treatment instrument occupies in a peripheral region around a central region in an image of at least one image signal among the left-eye image signal and the right-eye image signal; a blur region setting portion configured to, with respect to an image in the peripheral region that is disposed around an image in the central region in which blur processing is not performed, set a region in which to perform blur processing in accordance with an analysis result of the image analysis portion; an image compositing portion configured to composite and output a 3D image with respect to which blur processing is performed on the left-eye image and the right-eye image, respectively, in accordance with a synchronization adjustment result of the synchronization adjustment portion and a setting result of the blur region setting portion; wherein the image analysis portion includes: an image dividing portion configured to segment the peripheral region around the central region in the image that is obtained by the image signal that is inputted, to thereby divide the peripheral region into a predetermined number of regions; a color component analysis portion configured to analyze color components in each of the predetermined number of regions; an image edge component extraction portion configured to extract an edge component of a straight component in each of the regions; and a treatment instrument region evaluation portion configured to evaluate a size of a region that an image of the treatment instrument occupies in the peripheral region based on an analysis result of the color component analysis portion and an extraction result of the image edge component extraction portion.

2. The stereoscopic endoscopic image processing apparatus according to claim 1, wherein the at least one processor is further programmed to execute:
a blur information generation portion configured to generate, in accordance with an analysis result of the image analysis portion, information regarding a blur intensity at a time of performing blur processing on the image in the peripheral region and regarding the blur region that is set by the blur region setting portion.

3. The stereoscopic endoscopic image processing apparatus according to claim 2, wherein the image analysis portion includes: an innermost block region arithmetic portion configured to perform an arithmetic operation for detecting an innermost block region so that blocks of a region in which the image of the treatment instrument exists in an innermost region as a region on an innermost side in the peripheral region are detected as the innermost block region based on an evaluation result of the treatment instrument region evaluation portion; and an outermost block region arithmetic portion configured to perform an arithmetic operation for detecting an outermost block region so that blocks of a region in which the image of the treatment instrument exists in an outermost region as a region on an outermost side in the peripheral region are detected as the outermost block region based on an evaluation result of the treatment instrument region evaluation portion.

4. The stereoscopic endoscopic image processing apparatus according to claim 3, wherein the at least one processor is further programmed to execute:
a blur processing portion that is provided in the image compositing portion, and is configured to perform blur processing on each of the left-eye image and the right-eye image with the blur intensity in the blur region that is generated by the blur information generation portion; and
a compositing portion that is provided in the image compositing portion, and is configured to combine the left-eye image and the right-eye image that are each subjected to blur processing by the blur processing portion.

5. The stereoscopic endoscopic image processing apparatus according to claim 4, wherein the at least one processor is further programmed to execute:
a control portion configured to:
control so that the blur information generation portion sets the blur region in accordance with a proportion of a number of regions forming the innermost block region occupying in a total number of regions of the innermost region in accordance with an arithmetic operation result of the innermost block region arithmetic portion;
control so that the blur information generation portion sets the blur intensity in accordance with a proportion of a number of regions forming the outermost block region occupying in a total number of regions of the outermost region in accordance with an arithmetic operation result of the outermost block region arithmetic portion; and
control so that the blur processing portion performs blur processing with respect to each of the left-eye image and the right-eye image with the blur intensity in the blur region that is set by the blur information generation portion.

6. The stereoscopic endoscopic image processing apparatus according to claim 5, wherein the control portion:
performs control that sets the blur region so as to progressively extend from the outermost region to the innermost region side as a number of regions forming the innermost block region increases in accordance with arithmetic operation result of the innermost block region arithmetic portion, and
controls to set the blur intensity in the blur region so as to increase in steps as a number of regions forming the outermost block region increases in accordance with arithmetic operation result of the outermost block region arithmetic portion increases.

7. The stereoscopic endoscopic image processing apparatus according to claim 6, wherein:
the control portion takes only a first peripheral region in an image of one image signal among the left-eye image signal and the right-eye image signal as the peripheral region, and controls so as to set the blur region and the blur intensity in the first peripheral region, and
the control portion controls so as to apply the blur region and the blur intensity that are set for the first peripheral region, with respect to a second peripheral region in an image of another image signal among the left-eye image signal and the right-eye image signal.

8. The stereoscopic endoscopic image processing apparatus according to claim 5, wherein:
the control portion takes only a first peripheral region in an image of one image signal among the left-eye image signal and the right-eye image signal as the peripheral region, and controls so as to set the blur region and the blur intensity in the first peripheral region, and
the control portion controls so as to apply the blur region and the blur intensity that are set for the first peripheral region, with respect to a second peripheral region in an image of another image signal among the left-eye image signal and the right-eye image signal.

9. The stereoscopic endoscopic image processing apparatus according to claim 4, wherein the synchronization adjustment portion has a memory that temporarily stores an image of another image signal belonging to a same frame as an image of one image signal with respect to which analysis of a region that an image of a treatment instrument occupies is performed by the image analysis portion, and performs a synchronization adjustment so that a 3D image signal with respect to which blur processing by the blur processing portion is performed on the image of the one image signal and the image of the other image signal is outputted after a single frame period from a frame in which the one image signal is inputted.

10. The stereoscopic endoscopic image processing apparatus according to claim 4, wherein the stereoscopic endoscopic image processing apparatus is provided in a 3D monitor comprising a display screen that displays a 3D image that an observer observes using 3D glasses for stereoscopic vision.

11. The stereoscopic endoscopic image processing apparatus according to claim 4, wherein the stereoscopic endoscopic image processing apparatus is provided in a 3D mixer into which are inputted the left-eye image signal and the right-eye image signal that are generated based on output signals of left and right image pickup devices provided in the stereoscopic endoscope, respectively, and which outputs a 3D image signal to a 3D monitor that displays a 3D image.

12. The stereoscopic endoscopic image processing apparatus according to claim 4, wherein the blur information generation portion has an information storing portion that, in accordance with information regarding a proportion of the innermost block region that is calculated by the innermost block region arithmetic portion, and information regarding a proportion of the outermost block region that is calculated by the outermost block region arithmetic portion, stores the blur region and the blur intensity with respect to which the blur processing portion performs blur processing, respectively, or stores a look-up table that is associated with information of the blur intensity and the blur region.

13. The stereoscopic endoscopic image processing apparatus according to claim 4, wherein the at least one processor is further programmed to execute:
a control portion configured to:
control so that the blur information generation portion sets the blur region in accordance with a proportion of a number of regions forming the outermost block region occupying in a total number of regions of the outermost region in accordance with an arithmetic operation result of the outermost block region arithmetic portion, control so that the blur information generation portion sets the blur intensity in accordance with a proportion of a number of regions forming the outermost block region occupying in a total number of regions of the innermost region in accordance with an arithmetic operation result of the innermost block region arithmetic portion, and control so that the blur processing portion performs blur processing with respect to each of the left-eye image and the right-eye image with the blur intensity in the blur region that is set by the blur information generation portion.

14. The stereoscopic endoscopic image processing apparatus according to claim 13, wherein the control portion:
performs control that sets the blur region so as to progressively extend from the outermost region to the innermost region side as a number of regions forming the outermost block region increases in accordance with the arithmetic operation result of the outermost block region arithmetic portion, and
controls to set the blur intensity in the blur region so as to increase in steps as a number of regions forming the innermost block region increase in accordance with the arithmetic operation result of the innermost block region arithmetic portion.

15. The stereoscopic endoscopic image processing apparatus according to claim 4, wherein the image dividing portion divides the peripheral region so as to include a plurality of regions belonging to the innermost region that are provided so as to adjacently surround an outer side of the central region, and a plurality of regions belonging to the outermost region that are provided on an outermost side in the image so as to surround an outer side of the innermost region.

16. The stereoscopic endoscopic image processing apparatus according to claim 4, further comprising:
the stereoscopic endoscope comprising the left and right image pickup devices;
an image processing apparatus that performs image processing with respect to the left and right image pickup devices, and generates the left-eye image signal and the right-eye image signal;
a 3D mixer that generates a 3D image signal based on the left-eye image signal and the right-eye image signal that are generated by the image processing apparatus; and
a 3D monitor that displays a 3D image based on the 3D image signal that is outputted from the 3D mixer and is inputted to the 3D monitor;
wherein the 3D mixer or the 3D monitor comprises the synchronization adjustment portion and the image analysis portion.

17. The stereoscopic endoscopic image processing apparatus according to claim 4, wherein:
as the blur processing, the blur processing portion performs processing that, by causing color information of a blurring target pixel that is included in the blur region to gradually extend to pixels around the blurring target pixel within the blur region, spreads the color information of the blurring target pixel to the surrounding pixels.

* * * * *